(12) United States Patent
Cooper et al.

(10) Patent No.: US 11,606,940 B2
(45) Date of Patent: Mar. 21, 2023

(54) METHOD FOR PRODUCING AN ANIMAL COMPRISING A GERMLINE GENETIC MODIFICATION

(71) Applicant: Commonwealth Scientific and Industrial Research Organisation, Acton (AU)

(72) Inventors: Caitlin Ann Cooper, Grovedale (AU); Mark Leslie Tizard, Highton (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 0 days.

(21) Appl. No.: 15/750,605

(22) PCT Filed: Aug. 5, 2016

(86) PCT No.: PCT/AU2016/050714
§ 371 (c)(1),
(2) Date: Feb. 6, 2018

(87) PCT Pub. No.: WO2017/024343
PCT Pub. Date: Feb. 16, 2017

(65) Prior Publication Data
US 2019/0014757 A1    Jan. 17, 2019

(30) Foreign Application Priority Data
Aug. 7, 2015 (AU) ............................ 2015903164

(51) Int. Cl.
| C12N 15/00 | (2006.01) |
| C07H 21/02 | (2006.01) |
| A01K 67/027 | (2006.01) |
| C12N 15/90 | (2006.01) |
| C12N 9/22 | (2006.01) |
| C12N 15/88 | (2006.01) |

(52) U.S. Cl.
CPC ............ A01K 67/0275 (2013.01); C12N 9/22 (2013.01); C12N 15/88 (2013.01); C12N 15/90 (2013.01); A01K 2217/072 (2013.01); A01K 2227/30 (2013.01); A01K 2267/02 (2013.01); C07H 21/02 (2013.01); C12N 2310/20 (2017.05)

(58) Field of Classification Search
CPC ...... A01K 67/0275; C12N 9/22; C12N 15/88; C12N 15/90; C12N 2310/20; C07H 21/02
See application file for complete search history.

(56) References Cited

U.S. PATENT DOCUMENTS

| 5,266,106 A | 11/1993 | Winnick et al. |
| 7,732,571 B2 | 6/2010 | Lee et al. |
| 2002/0081614 A1 | 6/2002 | Case et al. |
| 2003/0021776 A1 | 1/2003 | Rebar et al. |
| 2003/0069173 A1 | 4/2003 | Hawley-Nelson et al. |
| 2006/0246567 A1 | 11/2006 | Rebar et al. |
| 2008/0040823 A1 | 2/2008 | Ventura et al. |
| 2008/0182332 A1 | 7/2008 | Cai et al. |
| 2010/0291048 A1 | 11/2010 | Holmes et al. |
| 2013/0123484 A1 | 5/2013 | Liu et al. |
| 2015/0072064 A1 | 3/2015 | Tyack |

FOREIGN PATENT DOCUMENTS

| WO | 91/000287 A1 | 1/1991 |
| WO | 96/22321 A1 | 7/1996 |
| WO | 96/31549 A1 | 10/1996 |
| WO | 96/037223 A1 | 11/1996 |
| WO | 1999/042569 A1 | 8/1999 |
| WO | 2002/057308 A2 | 7/2002 |
| WO | 2002/063293 A1 | 8/2002 |
| WO | 2003/024199 A2 | 3/2003 |
| WO | 2007/017759 A2 | 2/2007 |
| WO | 2007/062000 A2 | 5/2007 |
| WO | 2008/138072 A1 | 11/2008 |
| WO | 2011/017293 A2 | 2/2011 |
| WO | 2013/155572 A1 | 10/2013 |
| WO | 2014/138792 A1 | 9/2014 |
| WO | 2014/189628 A1 | 11/2014 |

OTHER PUBLICATIONS

Jaenisch et al., 2016, US 20160186208 A1, effective filing date, Apr. 16, 2013.*
Patil et al., 2011, Indian Journal of Public Health research & Development, vol. 2, No. 1, p. 106-109.*
Khodarovich et al., 2013, Applied Biochemistry and Microbiology, vol. 49, No. 9, pp. 711-722.*
Selsby et al., 2015, ILAR Journal, vol. 56, No. 1, p. 116-126.*
Yang et al., 2016, PNAS, 113(41), E6209-E6218, p. 1-10.*
Guo et al., 2015, Cell Research, vol. 25, p. 767-768.*
Lee et al., 2016, Drug Discovery Today: Disease Models, vol. 20, p. 13-20.*
Rapp, Jeffrey, 2011, US 20110014653 A1.*
Fahrenkrug et al., Mar. 5, 2015, US 20150067898 A1, effective filing date, Aug. 27, 2013.*
Quay et al., 2014, US 20140037714 A1.*
Doudna et al., 2014, US 20140068797 A1.*
Sung et al., 2014, Genome research, 24: 125-131.*
Aida et al., 2015 (Published Apr. 29, 2015), Genome Biology, 16:87, p. 1-11.*
Chau et al., 2020, Biochemical Society Transactions, 48: 357-365.*
International Preliminary Report on Patentability for PCT/AU2016/050714, 5 pages (dated Feb. 13, 2018).
International Search Report and Written Opinion of the International Searching Authority for PCT/AU2016/050714 (dated Sep. 29, 2016).

(Continued)

*Primary Examiner* — Shin Lin Chen
(74) *Attorney, Agent, or Firm* — Gary J. Gershik

(57) ABSTRACT

The present invention relates to methods for producing a non-human animal, such as an avian, comprising a targeted germline genetic modification, the method comprising: (i) delivering a programmable nuclease to sperm; (ii) fertilizing an ovum with the sperm, and (iii) generating the animal from the ovum, wherein the nuclease introduces the genetic modification into DNA of the sperm and/or the ovum.

12 Claims, 9 Drawing Sheets

Figure 1:
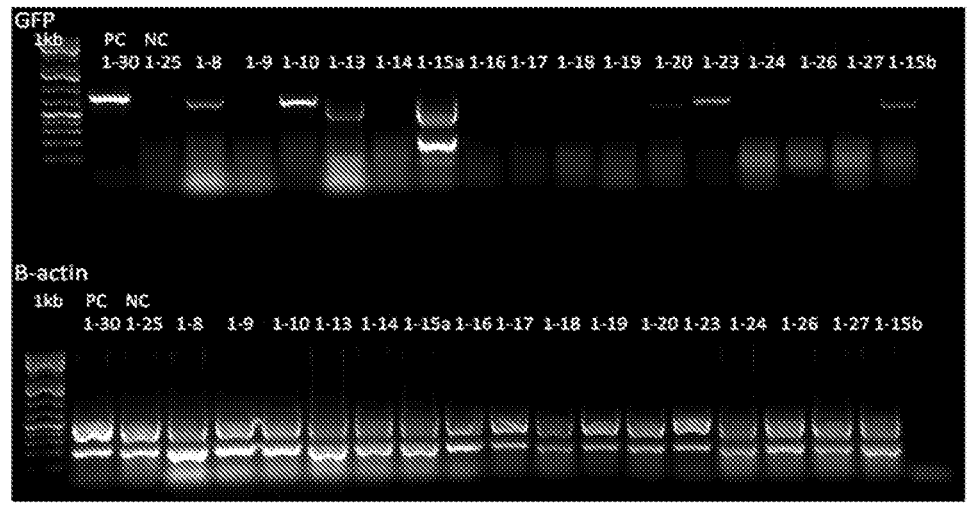
Figure 1:
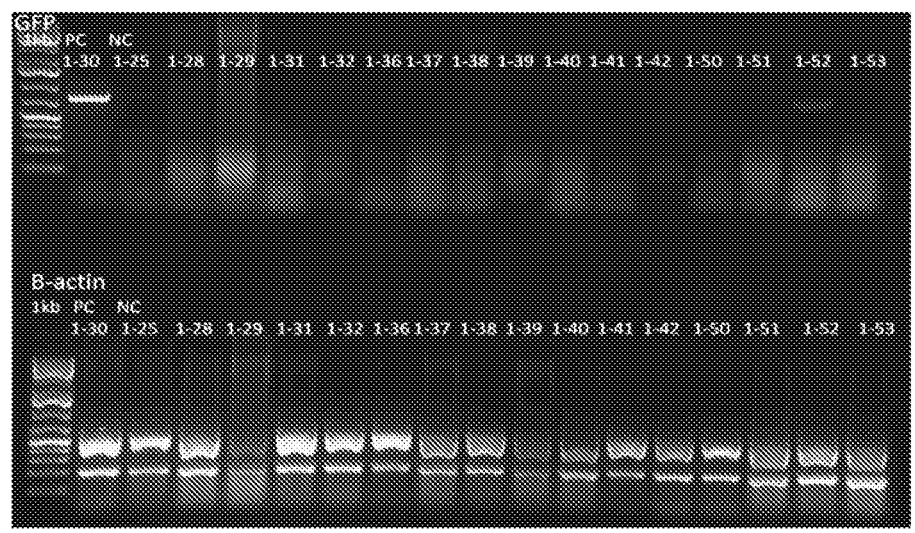
Figure 1:
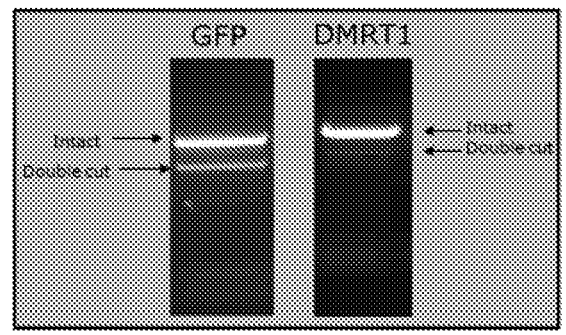

Specification includes a Sequence Listing.

(56) References Cited

OTHER PUBLICATIONS

Harel-Markowitz et al., "Use of Sperm Plasmid DNA Lipofection Combined with REMI (Restriction Enzyme-Mediated Insertion) for Production of Transgenic Chickens Expressing eGFP (Enhanced Green Fluorescent Protein) or Human Follicle-Stimulating Hormone1", Biology of Reproduction, 80: 1046-1052 (2009).
Zuo et al., "Site Directed Genome Knockout in Chicken Cell Line and Embryos Can Use CRISPR/Cas Gene Editing Technology", G3: Genes, Genomes, Genetics, 6: 1787-1792 (2016).
Extended European Search Report for corresponding European Patent Application No. 16834309.3 dated Jan. 3, 2019, 8 pages.
Ain, Q. et al., "Current and future delivery systems for engineered nucleases: ZFN, TALEN and RGEN", Journal of Controlled Release, 205: 120-127 (2015).
Balciunas, D., et al., "Harnessing a High Cargo-Capacity Transposon for Genetic Applications in Vertebrates", PLoS Genetics, 2(11): 1715-1724 (Nov. 2006).
Ball, B. et al., "Liposome-mediated uptake of exogenous DNA by equine spermatozoa and applications in sperm-mediated gene transfer", Equine Veterinary Journal, 40(1): 76-82 (2008).
Barrangou, R., "RNA-mediated programmable DNA cleavage", Nature Biotechnology, 30(9): 836-838 (Sep. 2012).
Carson, D. et al., "Efficient TALEN-mediated gene knockout in livestock", PNAS, 109(43): 17382-17387 (Oct. 2012).
Celebi, C. et al., "The Making of" Transgenic Spermatozoa, Biology of Reproduction, 68: 1477-1483 (2003).
Chapman, K. et al., "Targeted Germline Modifications in Rats Using CRISPR/Cas9 and Spermatogonial Stem Cells", Cell Reports, 10: 1828-1835 (Mar. 2015).
Collares, T. et al., "Transgene transmission in chickens by sperm-mediated gene transfer after seminal plasma removal and exogenous DNA treated with dimethylsulfoxide or N,N-dimethylacetamide", J. Biosci., 36(4): 612-620 (Sep. 2011).
Cong, L. et al., "Multiplex Genome Engineering Using CRISPR/Cas Systems", Science, 339(6121): 819-823 (Feb. 2013).
Davis, D. et al., "Zinc Finger Nucleases as tools to understand and treat human diseases", BMC Medicine, 8(42): 1-11 (2010).
Dhanapala, P. et al., "Cracking the egg: An insight into egg hypersensitivity", Molecular Immunology, 66: 375-383 (2015).
Dimitrov, L. et al., "Germline Gene Editing in Chickens by Efficient CRISPR-Mediated Homologous Recombination in Primordial Germ Cells", PLos One, 1-10 (2016).
Ding, S. et al., "Efficient Transposition of the piggyBac (PB) Transposon in Mammalian Cells and Mice", Cell, 122: 473-483 (2005).
Durai, S. et al., "Zinc finger nucleases: custom-designed molecular scissors for genome engineering of plant and mammalian cells", Nucleic Acids Research, 33(18): 5978-5990 (2005).
Gagne, M. et al., "Electroporation of Bovine Spermatozoa to Carry Foreign DNA in Oocytes", Molecular Reproduction and Development, 29: 6-15 (1991).
Gandolfi, F., "Sperm-Mediated Transgenesis", Theriogenology, 53: 127-138 (2000).
Garcia-Vazquez, F.A. et al., "Effect of sperm treatment on efficiency of EGFP-expressing porcine embryos produced by ICSI-SMGT", Theriogenology, 72: 506-518 (2009).
Haensler, J. et al., "Polymidoamine Cascade Polymers Mediate Efficient Transfection of Cells in Culture", Bioconjugate Chem., 4: 372-379 (1993).
Hamburger, V. et al., "A Seriers of Normal Stages in the Development of the Chick Embryo", Department of Zoology—Washington University/Iowa State College, 49-92 (1951).
Ivics, Z. et al., "Molecular Reconstruction of Sleeping Beauty, a Tc1-like Transposon from Fish, and Its Transposition in Human Cells", Cell, 91: 501-510 (Nov. 1997).
Kagami, H. et al., "The Development Origin of Primordial Germ Cells and the Transmission of the Donor-Derived Gametes in Mixed-Sex Germline Chimeras to the Offspring in the Chicken", Molecular Reproduction and Development, 48: 501-510 (1997).
Kawakami, K. et al., "identification of a functional transposase of the Tol2 element, an Ac-like element from the Japanese medaka fish, and its transposition in the zebrafish germ lineage", PNAS, 97(21): 11403-11408 (Oct. 2000).
Kim, H. et al., "A guide to genome engineering with programmable nucleases", Nature Reviews Genetics, 15: 321-334 (May 2014).
Laible, G. et al., "Improving livestock for agriculture—technological progress from random transgenesis to precision genome editing heralds a new era", Biotechnol. J., 10: 109-120 (2015).
Lake, P., "Fowl Semen as Collected by the Massage Method", Poultry Research Centre, Edinburgh, 1-8 (1957).
Lavitrano, M. et al., "Sperm Cells as Vectors for Introducing Foreign DNA into Eggs: Genetic Transmoration of Mice", Cell, 57: 717-723 (Jun. 1989).
Lavitrano, M. et al.,, "The Interaction Between Exogenous DNA and Sperm Cells", Molecular Reproduction and Development, 31: 161-169 (1992).
Li, F. et al., "Efficient genetic manipulation of the NOD-Rag1-/-IL2RagammacC-null mouse by combining in vitro fertilization and CRISPR/Cas9 technology", Scientific Reports, 4: 1-7 (2014).
Liang, P. et al., "CRISPR/Cas9-mediated gene editing in human tripronuclear zygotes", Protein Cell, 6(5): 363-372 (2015).
Maksimenko, O. et al.,, "Use of Transgenic Animals Biotechnology: Prospects and Problems", ACTA Naturae, 5(1): 33-46 (2013).
Nakade, S. et al., "Microhommology-mediated end-joining-dependent integration of donor DNA in cells and animals using TALENs and CRISPR/Cas9", Nature Communications, 1-8 (2014).
Nakanishi, A. et al., "Gene Transfer in the Chicken by Sperm-Mediated Methods", Molecular Reproduction and Developement, 36: 258-261 (1993).
Oishi, I. et al., "Targeted mutagenesis in chicken using CRISPR/Cas9 system", Scientific Reports, 1-10 (2016).
Park, T. et al., "Targeted gene knockout in chickens mediated by TALENs", PNAS, 111(35): 12716-12721 (Sep. 2014).
Pereyra-Bonnet, F. et al., "Efficiency of Sperm-Mediated Gene Transfer in the Ovine by Laparoscopic Insemination, In Vitro Fertilization and ICSI", Journal of Reproduction and Development, 57(2): 188-196 (2011).
Petitte, J., "The Avian Germline and Strategies for the Production of Transgenic Chickens", Journal of Poultry Science, 39: 205-228 (2002).
Petitte, J. et al., "The incredible, edible, and therapeutic egg", PNAS, 104(6): 1739-1740 (Feb. 2007).
Sato, T. et al., "Genome Editing in Mouse Spermatogonial Stem Cell Lines Using TALEN and Double-Nicking CRISPR/Cas9", Stem Cell Reports, 5: 75-82 (Jul. 2015).
Shemesh, M. et al., "Gene Integration Into Bovine Sperm Genome and Its Expression in Transgenic Offspring", Molecular Reproduction and Development, 56; 306-308 (2000).
Shen, W., et al., "Efficient and Simple Production of Transgenic Mice and Rabbits Using the New DMSO-Sperm Mediated Exogenous DNA Transfer Method", Molecular Reproduction and Development, 73: 589-594 (2006).
Smith, K. et al., "Sperm-mediated gene transfer: applications and implications", BioEssays, 27: 551-562 (2005).
Sullenger, B. et al., "Overexpression of TAR Sequences Renders Cells Resistant to Human Immunodeficiency Virus Replication", Cell, 63: 601-608 (Nov. 1990).
Tan, W. et al., "Efficient nonmeiotic allele introgression in livestock using custom endonucleases", PNAS, 110(41): 16526-16531 (Oct. 2013).
Tang, M. et al., "In Vitro Gene Delivery by Degraded Polyamidoamine Dendrimers", Bioconjugate Chem., 7: 703-714 (1996).
Veron, N. et al., "CRISPR mediated somatic cell genome engineering in the chicken", Developmental Biology, 407: 68-74 (2015).
Yang, C. et al., "Cock Spermatozoa Serve as the Gene Vector for Generation of Transgenic Chicken (Gallus gallus)*", Asian-Aust. j. Anim. Sci., 17(7): 885-891 (2004).
Zani, M. et al., "The Mechanism of Binding of Exogenous DNA to Sperm Cells: Factors Controlling the DNA Uptake", Experimental Cell Research, 217: 57-64 (1995).

(56) References Cited

OTHER PUBLICATIONS

Zekarias, B. et al., "Immunological basis of differences in disease resistance in the chicken", Vet. Res., 109-125 (2002).
Zhang, F. et al., "Programmable Sequence-Specific Transcriptional Regulation of Mammalian Genome using Designer TAL Effectors", Nat Biotechnol. 29(2): 149-153 (Feb. 2011).
Cooper, C. et al., "Developing knockout chickens in one generation via sperm transfection with PGE tools", Transgenic Research, 25(1): 119 (Feb. 2016).
Cooper, C. et al., "Generation of gene edited birds in one generation using sperm transfection assisted gene editing (STAGE)", Transgenic Research, 26(3): 331-347 (Nov. 2016).
Swain et al., "Can we edit sperm DNA before it meets egg?", NewScientist, Jul. 7, 2018, p. 9.

* cited by examiner

Figure 9

METHOD FOR PRODUCING AN ANIMAL COMPRISING A GERMLINE GENETIC MODIFICATION

This application is a U.S. National Stage Application under 35 U.S.C. § 371 of International Patent Application No. PCT/AU2016/050714 filed Aug. 5, 2016, which claims the benefit of priority to Australian Patent Application No. 2015903164 filed Aug. 7, 2015, the disclosures of all of which are hereby incorporated by reference in their entireties. The International Application was published in English on Feb. 16, 2017 as WO 2017/024343.

FIELD OF THE INVENTION

The present invention relates to methods for producing a non-human animal, such as an avian, comprising a targeted germline genetic modification.

BACKGROUND OF THE INVENTION

The overall goal in making a transgenic animal is the stable introduction of a genetic modification into the germline of the host animal that can be transmitted to offspring in a Mendelian fashion. By incorporating a genetic modification the characteristics of the animal can be specifically changed. Transgenic animals are generated for a variety of purposes. They can be used as basic research models, specialized non-agricultural purposes (such as pharmaceutical production or xenotransplantation) and also to enhance animal production traits and products. Accordingly, there is much interest in developing methods that increase the efficiency and specificity of the transgenic process in animals, particularly livestock animals including birds.

Transgenic and gene knockout avian species hold great potential for the poultry industry and medical community through increasing resistance to zoonotic diseases, reducing allergen potential of poultry products and generation of novel biomedical models. Using current methods of either culturing then transferring germ cells into embryos or direct injection of circulating germ cells in embryos to establish a breeding flock of transgenic birds takes two generations and the hatching and screening of hundreds of birds. This is time consuming and takes considerable resources and for many avian species no methodology for long term culture of germ cells exists. Finding a way to establish a breeding flock in one generation would save time, money, and significantly cut down on the number of birds used.

The current methods for producing transgenic chickens take two generations because in the first generation only a small percentage of the germ cell, or reproductive cells that eventually become the sperm and eggs, contain the desired transgene or knockout. This means that when you breed these animals only a small percentage of the next generation will have the desired trait. This is why hundreds of chicks must be hatched and screened to acquire enough transgenic birds to establish a breeding flock. Developing methodology to produce germline transgenic or gene edited birds in the first generation would save significant amounts of time and resources.

Previous studies have mixed sperm with a desired transgene DNA and a membrane binding agent and inseminated birds with the DNA and sperm mixture. This method is known as sperm mediated gene transfer (SMGT) and has had varying success in multiple species including mice, sheep, cattle, pigs, horses, and chickens (Lavitrano et al., 1989; Shemesh et al., 2000; Ball et al., 2008; García-Váquez et al., 2009; Collares et al., 2011; Pereyra-Bonnet et al., 2011). SMGT relies on random integration of the DNA through the non-homologous end joining (NHEJ) double stranded DNA break repair pathway. This is a largely inefficient, as even if random integration occurs it is not guaranteed to occur in an area of the genome that is favourable for gene expression and hundreds of birds are required in the first generation to produce a transgenic breeding flock.

There is a need to develop improved methods for producing an animal comprising a genetic modification, in particular methods that allow for targeted genetic modification at a predetermined location in the genome.

SUMMARY OF THE INVENTION

The present inventors have developed methods for introducing a germline genetic modification at a predetermined location in the genome of a non-human animal. The methods can be used to produce a non-human animal which has a targeted genetic modification in each cell of the animal.

In a first aspect the present invention provides a method for producing a non-human animal comprising a targeted germline genetic modification, the method comprising:
 (i) delivering a programmable nuclease to sperm,
 (ii) fertilizing an ovum with the sperm, and
 (iii) generating the animal from the fertilized ovum,
wherein the nuclease introduces the genetic modification into DNA of the sperm and/or the ovum.

In an embodiment, the method further comprises screening the animal obtained from step (iii) for the germline genetic modification. In an embodiment, the screening is PCR and/or sequencing of on a sample comprising DNA or RNA, such as germline cells, of the animal. In an embodiment, the screening determines if the animal is homozygous or heterozygous for the genetic modification.

In an embodiment, the programmable nuclease is delivered to the sperm in a composition comprising a transfection agent. In an alternate embodiment, the programmable nuclease is delivered to the sperm using electroporation.

In an embodiment, the programmable nuclease is selected from, but not necessarily limited to, an RNA-guided engineered nuclease (RGEN), transcription activator-like nuclease (TALEN), zinc-finger nuclease (ZFN) and an argonaute. In an embodiment, the programmable nuclease is an RNA-guided engineered nuclease (RGEN). In an embodiment, the RGEN nuclease is a clustered regularly interspaced short palindromic repeat-associated protein 9 (Cas9).

In an embodiment, the genetic modification results in reduced expression of one or more genes and/or proteins in the animal and/or progeny thereof.

In an embodiment, the genetic modification is a deletion, substitution or an insertion.

In an embodiment, the insertion is a transgene.

In an embodiment, step (ii) comprises artificially inseminating the sperm into a female animal.

In an embodiment, at least 1%, at least 5%, at least 10%, at least 20%, at least 23%, at least 24%, or at least 25%, or at least 26%, at least 30% or at least 40% of the animals produced using the method comprise the targeted germline genetic modification.

In an embodiment, all cells of the animal comprise the targeted germline genetic modification.

In an embodiment, the animal is heterozygous for the targeted germline genetic modification. However, in an alternate embodiment, the animal may be homozygous for the targeted germline genetic modification.

In an embodiment, the targeted germline genetic modification modifies a trait of the animal. Examples of traits which can be modified include, but are not limited to, susceptibility to disease such as an infectious disease, muscle development, skeletal development, allergenicity or sex. In an embodiment, the trait is sex/gender. In an embodiment, the germline genetic modification modifies the DMRT1 gene. In an embodiment, the trait is a production trait.

In an embodiment, the animal is a mammal. In an embodiment, the animal is a marsupial. In an embodiment, the animal is a monotreme. In an embodiment, the animal is a reptile. In an embodiment, the animal is a livestock animal such as a sheep, cow, pig, duck, chicken, goat or horse. In an embodiment, the animal is an avian. In an embodiment, the avian is selected from, but not necessarily limited to, a chicken, duck, turkey, goose, bantam or quail.

In an aspect, the present invention provides an animal produced by the method of the above aspect.

In a further aspect, the present invention provides a sperm produced by an animal of the invention.

In yet a further aspect, the present invention provides an ovum produced by an animal of the invention.

In an aspect, the present invention provides a method for producing a genetically modified animal, the method comprising:

(i) crossing a first animal of the invention with a second animal of the same species, and (ii) selecting progeny comprising the targeted germline genetic modification.

In an embodiment, the method comprises selecting progeny which are homozygous for the targeted germline genetic modification.

In an embodiment, the method comprises selecting progeny which are heterozygous for the targeted germline genetic modification.

In yet another aspect, the present invention provides an animal produced by the method of the above aspect.

In another aspect, the present invention provides a method of producing food, the method comprising:

(i) obtaining an animal of the invention, and (ii) producing food from the animal.

In an embodiment, the method comprises harvesting meat and/or eggs from the animal.

Any embodiment herein shall be taken to apply mutatis mutandis to any other embodiment unless specifically stated otherwise. For instance, as the skilled person would understand examples of the genetic modifications outlined above for the methods of the invention equally apply to the animals produced by the method of the invention.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1. PCRs for GFP and β-actin on WT phenotype embryos. A and B Embryo 1-30 served as a GFP expressing positive control with 1-25 serving as the negative control. PCRs for GFP and DMRT1 CRISPR mediated editing. C. PCR results from flow cytometer screened pools of cells targeted with 2 GFP CRISPR guides or 2 GFP CRISPR guides and 2 DMRT1 CRISPR guides. The larger intact size bands contain both intact unedited DNA and single guide cut DNA, while the lower bands contain DNA from cells where both guides cut a particular gene, which is referred to as a double cut.

Figure 2:
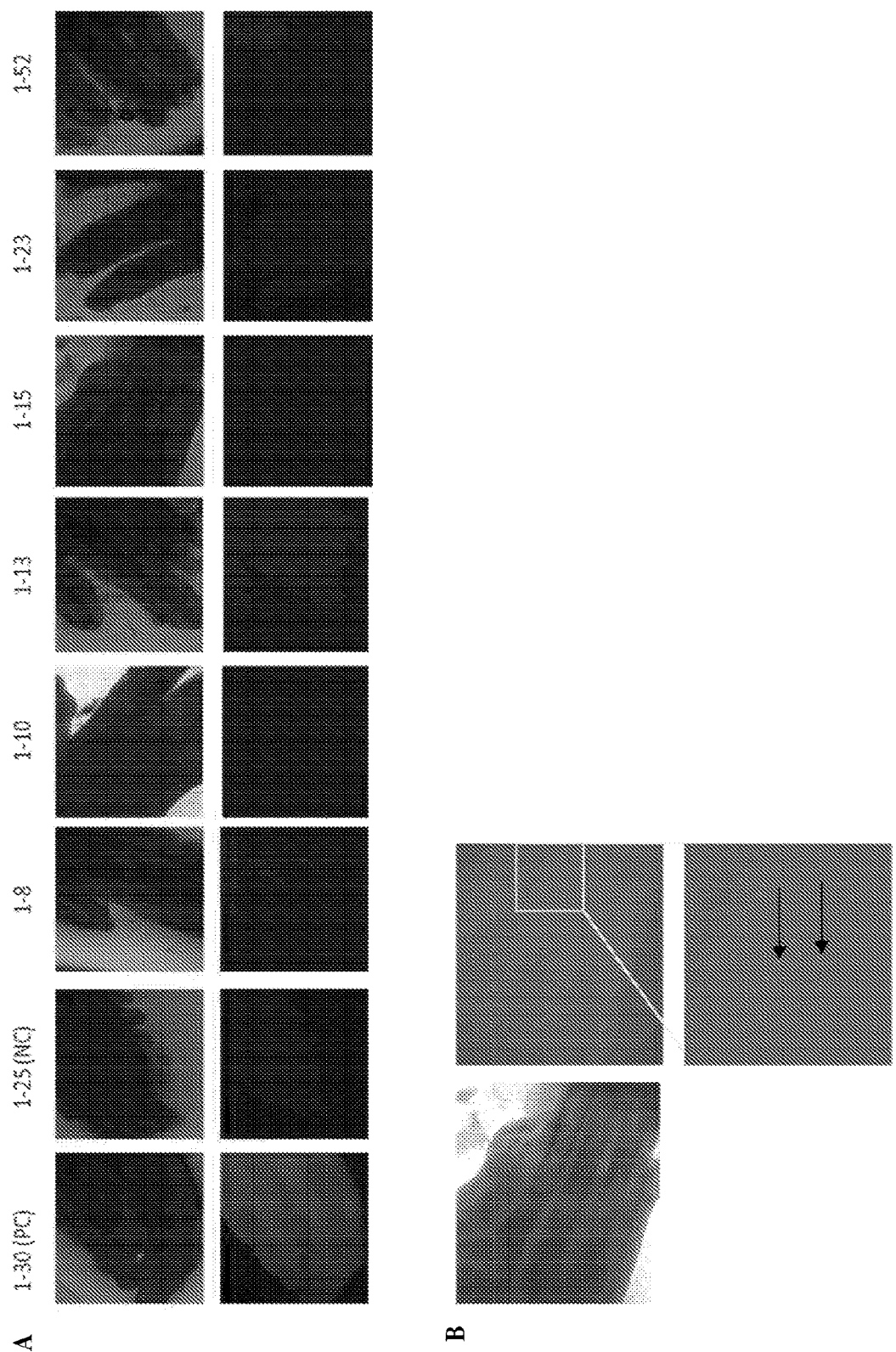

FIG. 2. Bright field and florescence microscopy of GFP PCR positive embryos. A. Embryo 1-30 is a GFP expressing positive control and 1-25 is a GFP PCR negative control. It can be seen that 1-8, 1-10, 1-13, 1-23, 1-52 do not express GFP. B Expanded bright field and florescence microscopy images of bird 1-15, which is chimeric for GFP expression (arrows indicate the small dots in the expanded panel).

Figure 3:

FIG. 3. GFP sequences. Inverted_pT2 is the plasmid used to generate the original GFP birds, I_30 is a GFP expressing embryo, and 1-10, 1-15, and 1-23 are GFP PCR positive embryos that have the WT phenotype (SEQ ID NOs 1 to 5 respectively). The boxs highlight the mutations seen in the ATG start site when comparing the plasmid and embryo controls to the WT phenotype embryos which harbor an A→G mutation. Boxes highlight mutations −10 and +24 of the start site.

Figure 4:
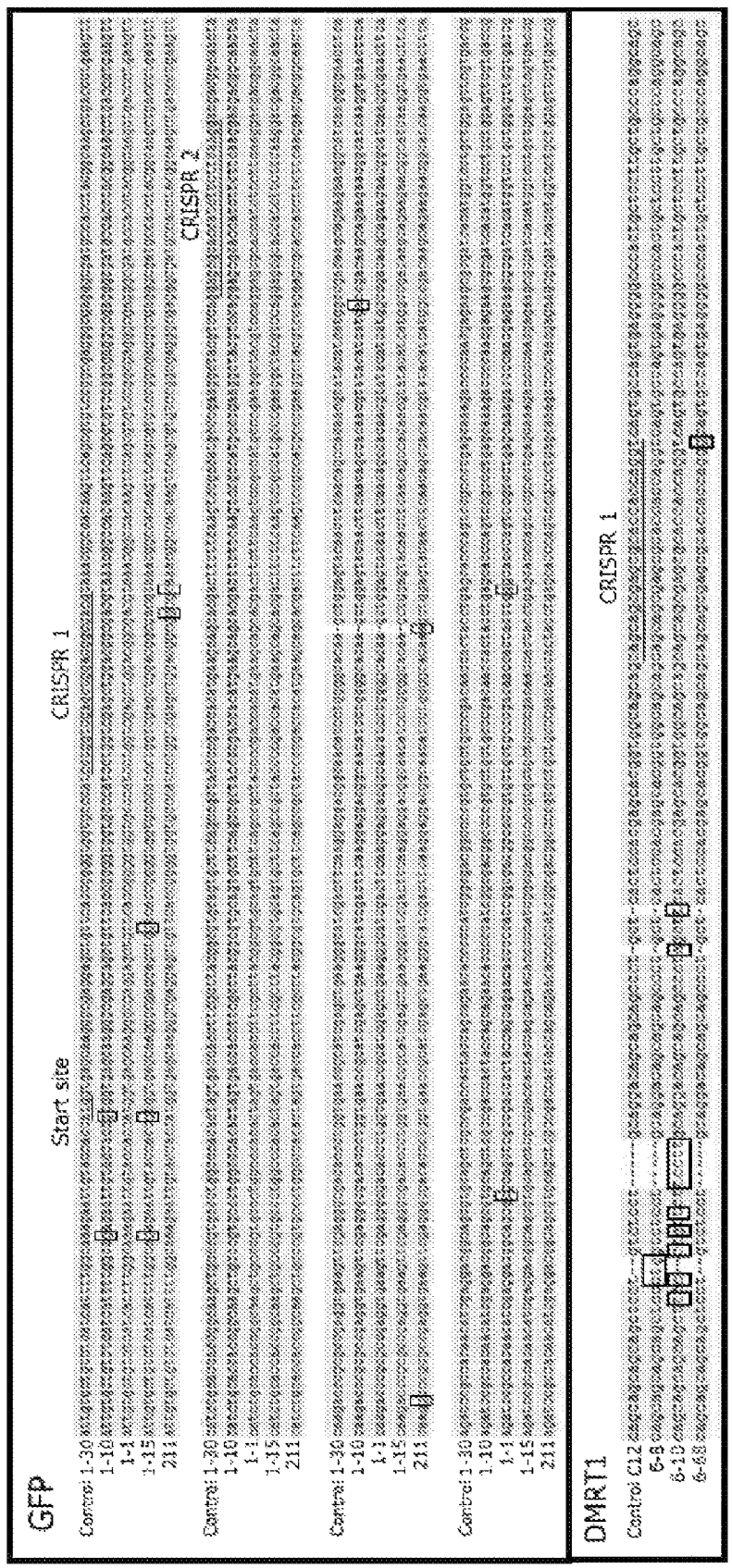

FIG. 4. GFP and DMRT1 sequences. Sequence alignment for selected samples from the GFP experiment and DMRT1 experiment to demonstrate the type of mutations seen and distance from the CRISPR sites.

Figure 5:
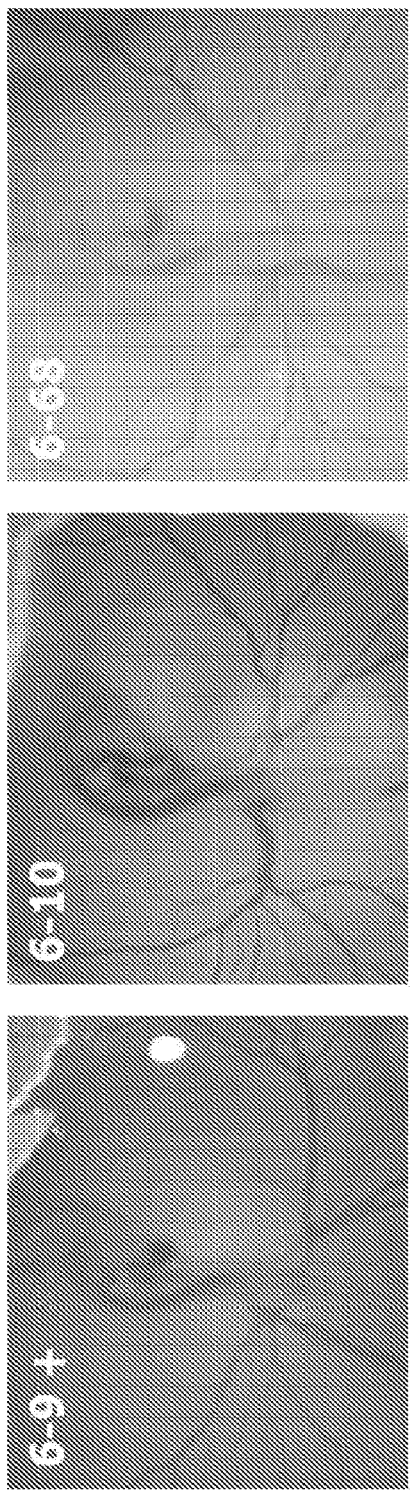

FIG. 5. Brightfield microscopy. Brightfield microscopy from day 2.5 embryos with mutations in DMRT1 as well as a non-mutated control.

Figure 6:
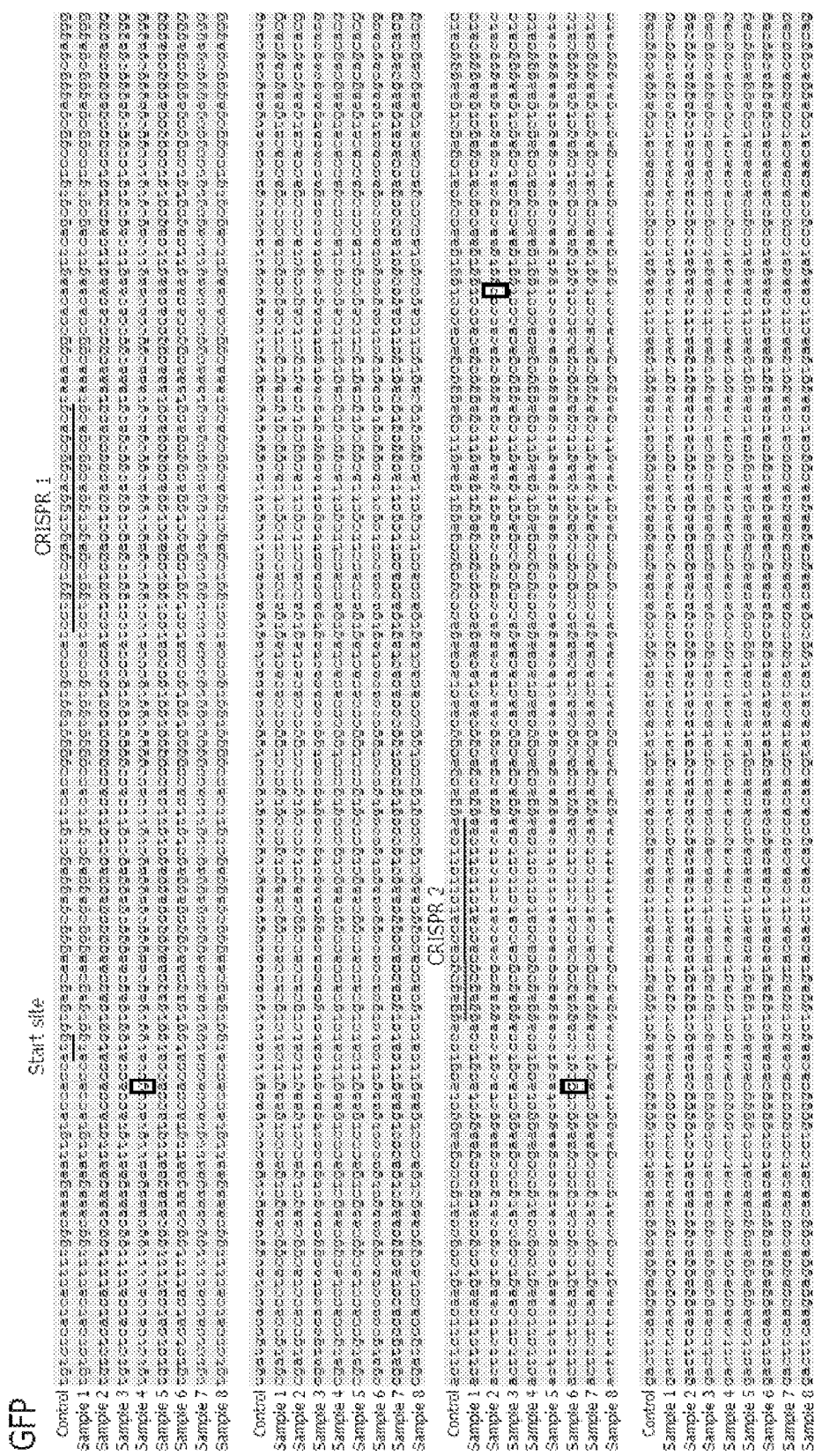

FIG. 6. Sequence alignment. The alignment shows intact GFP PCR products derived from cells in culture targeted with both GFP guides.

Figure 7:
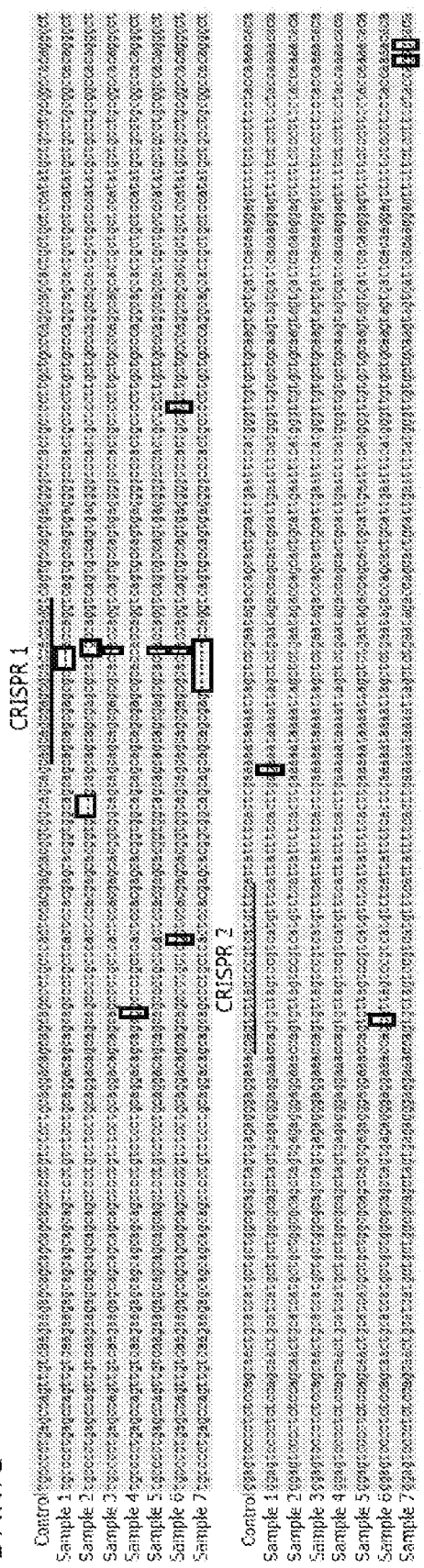

FIG. 7. Sequence alignment. The alignment shows intact DMRT1 PCR products derived from cells in culture targeted with both DMRT1 guides.

Figure 8:
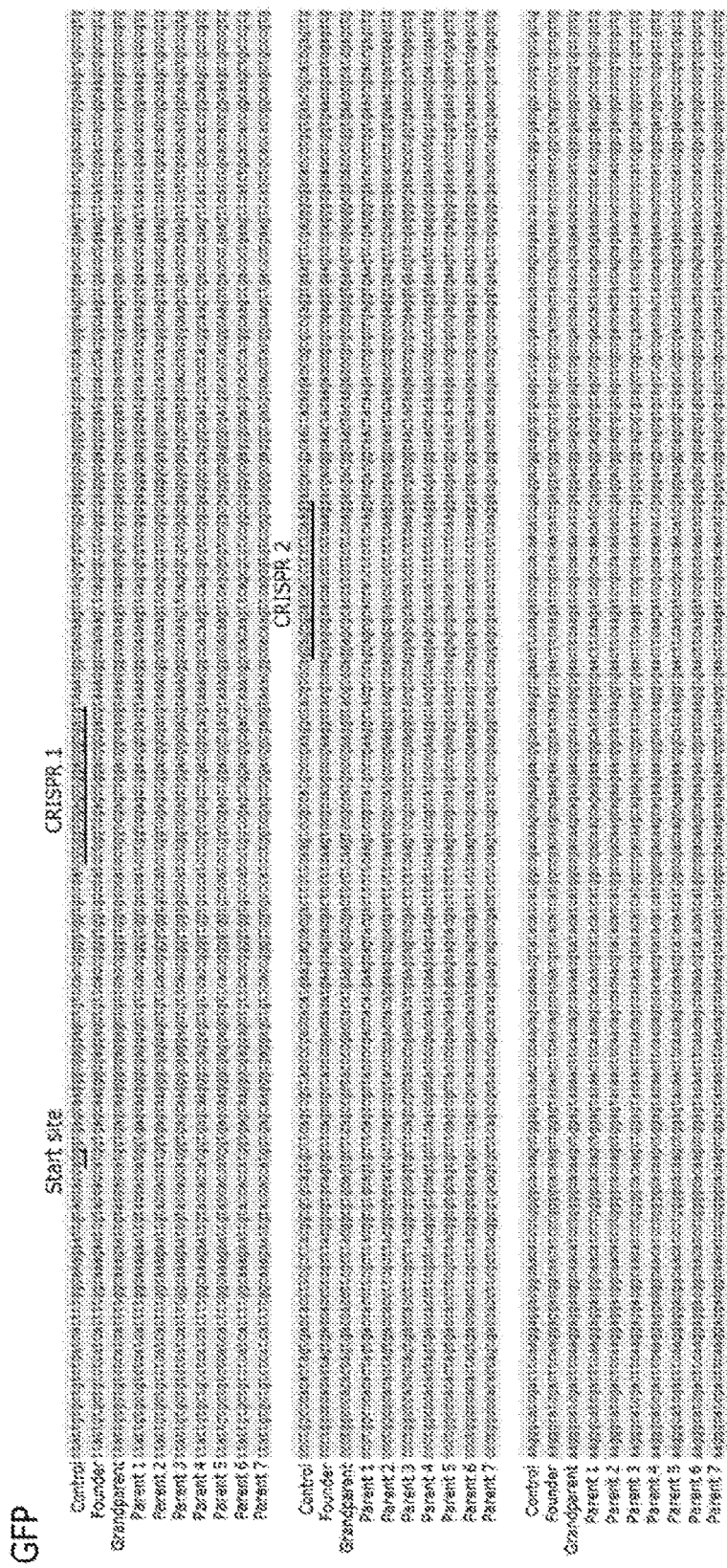

FIG. 8. Sequence alignment. The alignment shows the GFP gene from control samples including the founder mosaic rooster from the GFP line, the grandparental rooster, and all parental roosters used in the GFP experiment.

Figure 9:
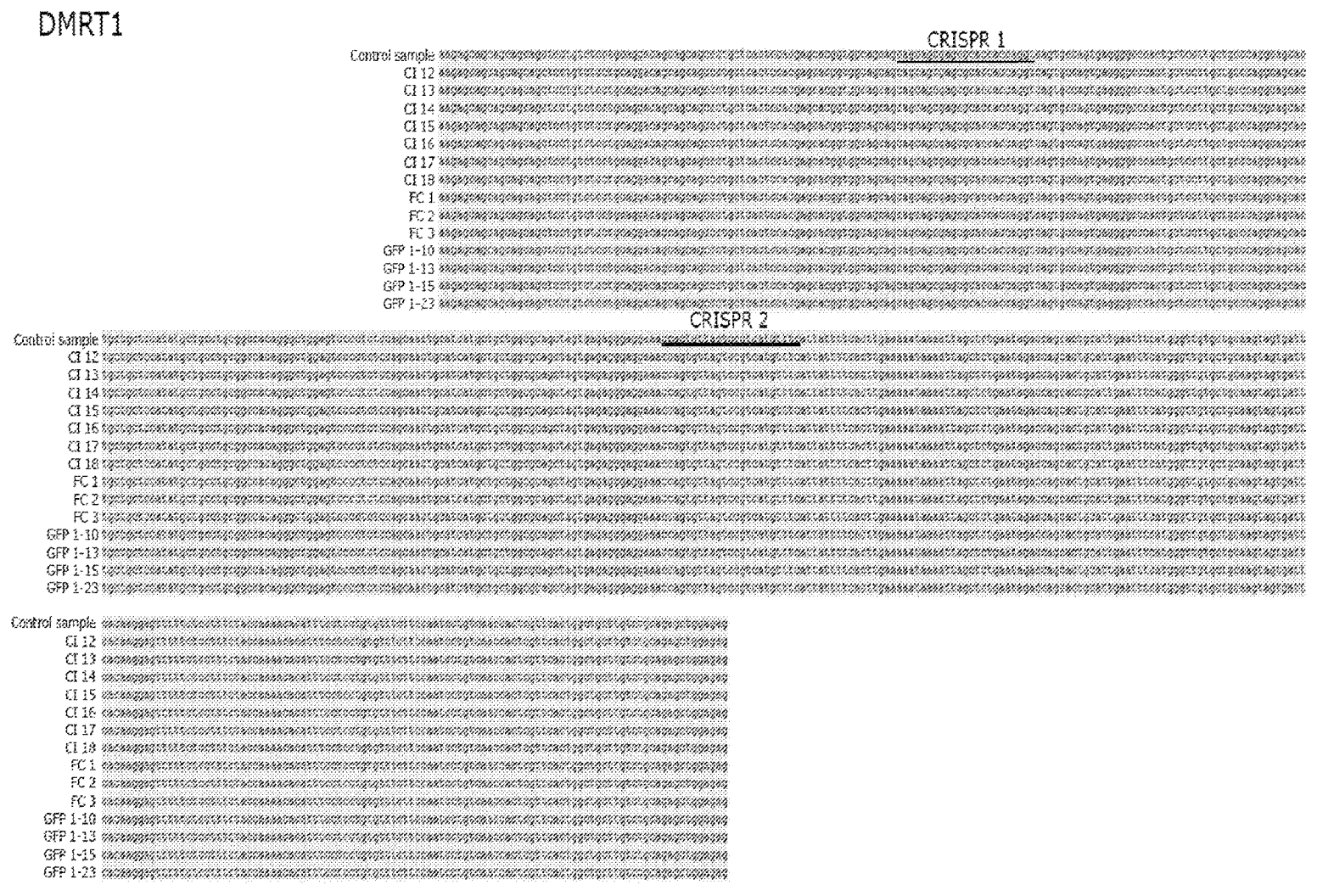

FIG. 9. Sequence alignment. The alignment shows the DMRT1 gene from control samples including samples from control in-seminations (CI), samples from fertile chickens (FC) and samples from the GFP experiment.

KEY TO THE SEQUENCE LISTING

SEQ ID NO:1—Region of inverted_pT2 plasmid used to generate GFP birds.

SEQ ID NO:2—Region corresponding to SEQ ID NO:1 from I_30 which is a GFP expressing embryo.

SEQ ID NO:3—Region corresponding to SEQ ID NO:1 from I_10 which is a GFP PCR positive embryo that has a WT phenotype.

SEQ ID NO:4—Region corresponding to SEQ ID NO:1 from I_15 which is a GFP PCR positive embryo that has a WT phenotype.

SEQ ID NO:5—Region corresponding to SEQ ID NO:1 from I_23 which is a GFP PCR positive embryo that has a WT phenotype.

SEQ ID NO:6—Guide RNA sg-GFP-1.
SEQ ID NO:7—Guide RNA sg-GFP-2.
SEQ ID NO:8—GFP PCR Primer FWD.
SEQ ID NO:9—GFP PCR Primer REV.
SEQ ID NO:10—B-actin PCR Primer FWD.
SEQ ID NO:11—B-actin PCR Primer REV.
SEQ ID NO:12—DMRT1 PCR Primer FWD.
SEQ OD NO:13—DMRT1 PCR Primer REV.
SEQ ID NO:14—Sex Test PCT Primer FWD.
SEQ ID NO:15—Sex Test PCR Primer REV.
SEQ ID NO:16—DMRT1 CRISPR Guide 1.
SEQ ID NO:17—DMRT1 CRISPR Guide 2.
SEQ ID NO:18—DMRT1 HDR Oligo.
SEQ ID NO: 19—FIG. 4 GFP Sample 1-30 (control).
SEQ ID NO: 20—FIG. 4 GFP Sample 1-10.
SEQ ID NO: 21—FIG. 4 GFP Sample 1-1.
SEQ ID NO: 22—FIG. 4 GFP Sample 1-15.
SEQ ID NO: 23—FIG. 4 GFP Sample 211.
SEQ ID NO: 24—FIG. 4 DMRT-1 Sample C-12 control.
SEQ ID NO: 25—FIG. 4 DMRT-1 Sample 6-8.
SEQ ID NO: 26—FIG. 4 DMRT-1 Sample 6-10.
SEQ ID NO: 27—FIG. 4 DMRT-1 Sample 6-68.
SEQ ID NO: 28—FIG. 6 Control GFP.
SEQ ID NO: 29—FIG. 6 Sample 1.
SEQ ID NO: 30—FIG. 6 Sample 2.
SEQ ID NO: 31—FIG. 6 Sample 3.
SEQ ID NO: 32—FIG. 6 Sample 4.
SEQ ID NO: 33—FIG. 6 Sample 5.
SEQ ID NO: 34—FIG. 6 Sample 6.
SEQ ID NO: 35—FIG. 6 Sample 7.
SEQ ID NO: 36—FIG. 6 Sample 8.
SEQ ID NO: 37—FIG. 7 DMRT1 Control.
SEQ ID NO: 38—FIG. 7 Sample 1.
SEQ ID NO: 39—FIG. 7 Sample 2.
SEQ ID NO: 40—FIG. 7 Sample 3.
SEQ ID NO: 41—FIG. 7 Sample 4.
SEQ ID NO: 42—FIG. 7 Sample 5.
SEQ ID NO: 43—FIG. 7 Sample 6.
SEQ ID NO: 44—FIG. 7 Sample 7.
SEQ ID NO: 45—FIG. 8 Sample Founder.
SEQ ID NO: 46—FIG. 8 Sample Grandparent.
SEQ ID NO: 47—FIG. 8 Sample Parent 1.
SEQ ID NO: 48—FIG. 8 Sample Parent 2.
SEQ ID NO: 49—FIG. 8 Sample Parent 3.
SEQ ID NO: 50—FIG. 8 Sample Parent 4.
SEQ ID NO: 51—FIG. 8 Sample Parent 5.
SEQ ID NO: 52—FIG. 8 Sample Parent 6.
SEQ ID NO: 53—FIG. 8 Sample Parent 7.
SEQ ID NO: 54—FIG. 9 Sample CI-12.
SEQ ID NO: 55—FIG. 9 Sample CI-13.
SEQ ID NO: 56—FIG. 9 Sample CI-14.
SEQ ID NO: 57—FIG. 9 Sample CI-15.
SEQ ID NO: 58—FIG. 9 Sample CI-16.
SEQ ID NO: 59—FIG. 9 Sample CL-17.
SEQ ID NO: 60—FIG. 9 Sample CI-18.
SEQ ID NO: 61—FIG. 9 Sample FC1.
SEQ ID NO: 62—FIG. 9 Sample FC2.
SEQ ID NO: 63—FIG. 9 Sample FC3.
SEQ ID NO: 64—FIG. 9 Sample 1-10.
SEQ ID NO: 65—FIG. 9 Sample 1-13.
SEQ ID NO: 66—FIG. 9 Sample 1-15.
SEQ ID NO: 67—FIG. 9 Sample 1-23.

DETAILED DESCRIPTION OF THE INVENTION

General Techniques and Selected Definitions

Unless specifically defined otherwise, all technical and scientific terms used herein shall be taken to have the same meaning as commonly understood by one of ordinary skill in the art (e.g., in cell culture, molecular genetics, recombinant DNA biology, transgenic animals, and biochemistry).

Unless otherwise indicated, the cell culture and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al., (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al., (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein, the term about, unless stated to the contrary, refers to +/−10%, more preferably +/−5%, more preferably +/−2.5%, even more preferably +/−1%, of the designated value.

As used herein, the term "avian" refers to any species, subspecies or race of organism of the taxonomic Class Aves, such as, but not limited to, such organisms as chicken, turkey, duck, goose, quail, game hen, squab, guinea fowl, pheasants, parrots, finches, hawks, crows and ratites including ostrich, emu and cassowary. The term includes the various known strains of *Gallus gallus* (chickens), for example, White Leghorn, Brown Leghorn, Barred-Rock, Sussex, New Hampshire, Rhode Island, Australorp, Cornish, Minorca, Amrox, California Gray, Italian Partidge-coloured, as well as strains of turkeys, pheasants, quails, duck, ostriches and other poultry commonly bred in commercial quantities.

The term "poultry" includes all avians kept, harvested, or domesticated for meat or eggs, for example chicken, turkey, ostrich, game hen, squab, guinea fowl, pheasant, quail, duck, goose, and emu.

Non-Human Animals with a Targeted Germline Genetic Modification

The present invention relates to methods for producing a non-human animal, such as an avian, comprising a targeted germline genetic modification. As used herein, the term "targeted germline genetic modification" refers to any genetic modification, such as but not limited to deletion, substation or insertion, made by way of human intervention at a predetermined location in the genome.

As used herein, a "genetically modified animal" refers to any animal in which one or more, preferably all, cells of the animal contains the targeted germline genetic modification.

In one embodiment, the genetic modification results in reduced expression of one or more genes and/or proteins in the animal and/or progeny thereof. Thus, in this embodiment, a gene knockout animal can be produced. As used herein, "reduced expression" of one or more genes and/or proteins is meant that the translation of a polypeptide and/or transcription of a gene in the cells of an animal produced using the methods of the invention, or progeny thereof, is reduced at least 10%, or at least 20%, or at least 30%, or at least 40%, or at least 50%, or at least 60%, or at least 70%, or at least 80%, or at least 90%, or at least 95%, or at least 98%, or at least 99%, or 100% relative to an isogenic animal lacking the genetic modification.

In an alternate embodiment, the genetic modification is the insertion of a transgene. The ability to target the transgene to a site of interest can be beneficial in that the transgene is interested at a site known or suspected to not cause any deleterious effects on the animal. The transgene may encode any functional protein or polynucleotide (such as an antisense polynucleotide or a dsRNA for RNAi). In an embodiment, the transgene encodes a protein which is expressed in the animal. In an embodiment, the transgene encodes a therapeutic protein such as an antibody.

In an embodiment, the transgene comprises one or more regulatory (promoter) elements operably linked to an open reading frame of interest (such as encoding a protein). "Operably linked" as used herein refers to a functional relationship between two or more nucleic acid (e.g., DNA) segments. Typically, it refers to the functional relationship of a transcriptional regulatory element to a transcribed sequence. For example, a promoter is operably linked to a coding sequence, such as an open reading frame encoding, if it stimulates the transcription of the coding sequence in an appropriate cell. Generally, promoter transcriptional regulatory elements that are operably linked to a transcribed sequence are physically contiguous to the transcribed sequence, i.e., they are cis-acting.

The transgene may also comprise a 3' non-translated sequence, for example from about 50 to 1,000 nucleotide base pairs, which may include a transcription termination sequence. A 3' non-translated sequence may contain a transcription termination signal which may or may not include a polyadenylation signal and any other regulatory signals capable of effecting mRNA processing.

In an embodiment, the targeted germline genetic modification is in a sex chromosome. In an alternate embodiment, the targeted germline genetic modification is a somatic chromosome.

In one embodiment, the genetic modification is at least introduced into the DNA of the sperm.

In another embodiment, the genetic modification is at least introduced into the DNA of the fertilized ovum (at the single cell stage). As the skilled person will appreciate, in this embodiment the genetic modification may be introduced into either the maternal or paternal derived DNA, or both. Generally, it is expected that the paternal DNA will be modified more frequently since the sperm will most likely be exposed to the nuclease for a longer period. An example of an exception is where the genetic modification targets a gene only present in the female chromosome of the animal, such as the W chromosome of an avian.

In an embodiment, all cells of the animal comprise the targeted germline genetic modification.

In some instances, not all of the cells of an animal produced using the methods of the invention, including not all the germline cells, will have the genetic modification. In these circumstances, the nuclease has probably introduced the genetic modification after the fertilized ovum has begun to divide. Such animals produced using the methods of the present invention can readily be identified, and excluded from further breeding, using routine techniques such as PCR and/or DNA sequencing analysis of germline cells for the targeted genetic modification.

Animals produced using the methods of the invention can be screened for the presence of the targeted germline genetic modification. This can step can be performed using any suitable procedure known in the art. For instance, a nucleic acid sample, such as a genomic DNA sample, can be analysed using standard DNA amplification and sequencing procedures to determine if the genetic modification is present at the targeted site (locus) in the genome.

In an embodiment, the screening also determines whether the animal is homozygous or heterozygous for the genetic modification.

In another embodiment, the animal is screened to identify whether the genetic modification can be found in germline cells such that it can be passed on to its offspring.

Production of Non-Human Animals with a Targeted Germline Genetic Modification

The present invention provides a method for producing a non-human animal comprising a targeted germline genetic modification, the method comprising:
 (i) delivering a programmable nuclease to sperm,
 (ii) fertilizing an ovum with the sperm, and
 (iii) generating the animal from the fertilized ovum.

The present invention also provides a method of producing sperm comprising a targeted germline genetic modification, the method comprising delivering a programmable nuclease to sperm, wherein the nuclease introduces the genetic modification into DNA of the sperm.

The present invention also provides a method of producing an ovum comprising a targeted germline genetic modification, the method comprising:
 (i) delivering a programmable nuclease to sperm, and
 (ii) fertilizing an ovum with the sperm, wherein the nuclease introduces the genetic modification into DNA of the ovum.

Delivering a Programmable Nuclease to Sperm

The programmable nuclease can be delivered to the sperm in vitro or in vivo, preferably in vitro. As the skilled person would appreciate, the term "sperm" as used in the context of the invention is typically used in the plural sense and thus millions of individual sperm cells will be present when performing the invention.

Methods of collecting sperm from an animal are well known. For instance, three commonly used techniques for collecting semen are the use of an artificial vagina, digital manipulation and electroejaculation. The technique used depends on the species being collected and the disposition of the individual male.

In an embodiment, the seminal plasma is removed from the sperm prior to the addition of the programmable nuclease to be delivered. In an embodiment, the seminal plasma is removed by washing, for example in the presence of a semen extender.

Semen extender is a liquid diluent which is added to semen to preserve its fertilizing ability. It acts as a buffer to protect the sperm cells from their own toxic by-products, and it protects the sperm cells from cold shock and osmotic shock during the chilling and shipping process (the sperm is chilled to reduce metabolism and allow it to live longer). Special freezing extender use also allows cryogenic preservation of sperm ("frozen semen"), which may be transported for use, or used on-site at a later date. As the skilled person would appreciate, many different semen extenders are available from commercial suppliers such as MOFA Global (Verona, Wis., USA) and Minitube (Tiefenbach, Germany).

The sperm may be stored, for instance at 4° C. or cryopreserved, before being used for the invention.

Methods for delivering the programmable nuclease include, but are not limited to, the use of transfection agents, electroporation and bolistics (i.e., loading the nucleic acid onto gold or other metal particles and shooting or injecting into the cells).

Electroporation is a technique in which an electrical field is applied to cells in order to increase the permeability of the cell membrane, allowing chemicals, drugs, or DNA to be introduced into the cell. Several hundred volts across a distance of several millimeters are typically used in this process. The skilled person can readily use standard trial and error experiments to determine the optimal electroporation conditions for a given sperm sample. An example of how bovine sperm can be electroporated is described in Gagne et al. (1991), whereas an example of how chicken sperm can be electroporated is described in Nakanishi and Iritani (1993).

The term "transfection agent" as used herein refers to a composition for enhancing the uptake of the programmable nuclease into the sperm. While any transfection agent known in the art to be suitable for transfecting eukaryotic cells may be used, the present inventors have found that transfection agents comprising a cationic lipid are particularly useful in the methods of the present invention.

In an embodiment, monovalent cationic lipids are selected from one or more of DOTMA (N-[1-(2.3-dioleoyloxy)-propyl]-N,N,N-trimethyl ammonium chloride), DOTAP (1,2-bis(oleoyloxy)-3-3-(trimethylammonium)propane), DMRIE (1,2-dimyristyloxypropyl-3-dimethyl-hydroxy ethyl ammonium bromide) or DDAB (dimethyl dioctadecyl ammonium bromide). Preferred polyvalent cationic lipids are lipospermines, specifically DOSPA (2,3-dioleoyloxy-N-[2(sperminecarboxamido)ethyl]-N,N-dimethyl-1-propan-amin-iumtrifluoro-acetate) and DOSPER (1,3-dioleoyloxy-2-(6carboxy spermyl)-propyl-amid, and the di- and tetra-alkyl-tetra-methyl spermines, including but not limited to TMTPS (tetramethyltetrapalmitoylspermine), TMTOS (tetramethyltetraoleylspermine), TMTLS (tetramethyltetralaurylspermine), TMTMS (tetramethyltetramyristylspermine) and TMDOS (tetramethyldioleylspermine). Cationic lipids are optionally combined with non-cationic lipids, particularly neutral lipids, for example lipids such as DOPE (dioleoylphosphatidylethanolamine), DPhPE (diphytanoylphosphatidylethanolamine) or cholesterol. A cationic lipid composition composed of a 3:1 (w/w) mixture of DOSPA and DOPE or a 1:1 (w/w) mixture of DOTMA and DOPE are generally useful in the methods of the invention. Non-limiting examples of suitable commercially available transfection agents comprising cationic lipids include Lipofectamine (Life Technologies) and Lipofectamine 2000 (Life Technologies).

Dendrimers, such as of generation 5 or higher (G5 or higher), can be used as a transfection agent with those of generation between G5-G10 being of particular interest. Dendrimers that may be useful in the invention include those with NH3 or ethylenediamine cores, GX(NH3) or GX(EDA), where X=the generation number. Dendrimers where X=5-10 being preferred. Dendrimers that may be useful in the invention include those in which the repeating unit of the internal layers is a amidoamine (to form polyamidoamines, i.e. PAMAMs). Useful dendrimers include those in which the terminal functional groups at the outer surface of the dendrimer provides a positive charge density, e.g., as with terminal amine functional groups. The surface charge and the chemical nature of the outer dendrimer surface can be varied by changing the functional groups on the surface, for example, by reaction of some or all of the surface amine groups. Of particular interest are dendrimers that are functionalized by reaction with cationic amino acids, such as lysine or arginine. Grafted dendrimers as described, for example in WO 96/22321 and WO 96/31549 and noted in U.S. Pat. No. 5,266,106, can be employed in methods of this invention. Activated dendrimers (Haensler and Szoka, 1993; Tang et al., 1996) can also be employed in methods of the invention.

Other examples of transfection agents include dimethyl sulfoxide DMSO and Triton-X.

The transfection agent may further comprise peptide sequences from viral, bacterial or animal proteins and other sources, including peptides, proteins or fragments or portions thereof that can enhance the efficiency of transfection of eukaryotic cells mediated by transfection agents, including cationic lipids and dendrimers. Such peptides are described in US20030069173 and include, for example, viral peptides or proteins of influenza virus, adenovirus, Semliki forest virus, HIV, hepatitis, herpes simplex virus, vesicular stomatitis virus or simian virus 40 and more specifically an RGD-peptide sequence, an NLS peptide sequence and/or a VSVG-peptide sequence and to modified peptides or proteins of each of the foregoing.

The programmable nuclease may be mixed (or "complexed") with the transfection agent according to the manufacturer's instructions or known protocols. In instances where the programmable nuclease is programmed for example by one or more RNA, DNA and hybrid RNA/DNA sequences, both the programmable nuclease and one or more programming sequences may be mixed (or "complexed") with the transfection agent independently or together according to the manufacturer's instructions or known protocols. By way of example, when transfecting a programmable nuclease programmed by one or more sequences physically separate from the nuclease 30 μL of Lipofectamine 2000 CD transfection agent (Invitrogen, Life Technologies) can be combined with 200 μL of Opti-Pro media. Cas9 mRNA (8 μg) can be combined with 100 μl of Opti-Pro media. About 4 μg guide RNA (gRNA) can be combined with 100 μl of Opti-Pro media. 115 μl of the lipofectamine 2000 CD+ Opti-Pro media solution can be added separately to the mRNA and gRNA mixtures. Resulting mixtures can then be incubated at room temperature for 5 to 30 minutes. A suitable volume of the transfection mixture can then be delivered to the sperm. The person skilled in the art will appreciate that the protocols for mixing the transfection agent and programmable nuclease, as well as delivery to the sperm, may be optimised in light of the teachings of the present specification.

In an embodiment, the programmable nuclease and sperm are incubated in the composition comprising a transfection agent for at least 5, or at least 10, or at least 15, or at least 20, or at least 25, or at least 30 minutes before fertilizing an ovum(ova) with the sperm.

Fertilizing an Ovum with the Sperm

The step of fertilizing the ovum (often referred to in the art as an egg) with the sperm can be performed using any standard fertilization procedure. The ovum may be fertilized in vitro (namely in vitro fertilization) and then implanted into a female animal (which may or may not be the source of the ovum). The fertilized ovum (zygote) may be cultured for a short period to produce a blastocyst which is then implanted into the female animal. Alternatively, the ovum may be fertilized in vivo by inseminating the female animal with sperm comprising the programmable nuclease (namely artificial insemination).

The step may use a single ovum or multiple ova.

Procedures for the in vitro fertilization and the artificial insemination of non-human animals are well known in the art.

Generating Genetically Modified Animals

The female comprising the fertilized ovum is allowed to gestate normally and give birth to offspring. As described herein, the offspring can be screened for the genetic modification using standard techniques known in the art.

The offspring may be allowed to mature and used for breeding progeny comprising the targeted genetic modification. In one embodiment, the animal produced using the programmable nuclease is heterozygous for the genetic modification. In this instance, in a preferred embodiment the (first) animal is crossed with a second animal of the same species which also heterozygous for the targeted genetic modification. In this instance, the first and second animals may be brother and sister, or may be result of producing animals using the method of the invention using two different parent female animals. Typically in this example the offspring are screened to identify offspring which are heterozygous for the targeted genetic modification.

As the skilled addressee will appreciate, in some animals multiple offspring are produced by the same parent (or surrogate). In an embodiment, multiple different parent (or surrogate) animals are used when performing the invention.

Programmable Nucleases

As used herein, the term "programmable nuclease" relates to nucleases that can be "targeted" ("programmed") to recognize and edit a pre-determined site in a genome.

When delivered to sperm in accordance with the invention the nuclease has been suitably programmed such that it is capable of introducing a genetic modification into DNA of the sperm and/or the ovum (once the sperm has been used to fertilize the ovum).

In an embodiment, the programmable nuclease can induce site specific DNA cleavage at the pre-determined. In an embodiment, the programmable nuclease may be programmed to recognize a genomic location with a DNA binding protein domain, or combination of DNA binding protein domains. In an embodiment, the programmable nuclease may be programmed to recognize a genomic location by a combination of DNA-binding zinc-finger protein (ZFP) domains. ZFPs recognize a specific 3-bp in a DNA sequence, a combination of ZFPs can be used to recognize a specific a specific genomic location. In an embodiment, the programmable nuclease may be programmed to recognize a genomic location by transcription activator-like effectors (TALEs) DNA binding domains. In an alternate embodiment, the programmable nuclease may be programmed to recognize a genomic location by one or more RNA sequences. In an alternate embodiment, the programmable nuclease may be programmed by one or more DNA sequences. In an alternate embodiment, the programmable nuclease may be programmed by one or more hybrid DNA/RNA sequences. In an alternate embodiment, the programmable nuclease may be programmed by one or more of an RNA sequence, a DNA sequences and a hybrid DNA/RNA sequence.

Programmable nucleases that can be used in accordance with the present disclosure include, but are not limited to, RNA-guided engineered nuclease (RGEN) derived from the bacterial clustered regularly interspaced short palindromic repeat (CRISPR)-cas(CRISPR-associated) system, zinc-finger nuclease (ZFN), transcription activator-like nuclease (TALEN), and argonautes.

In an embodiment, the programmable nuclease is a Clustered Regularly Interspersed Short Palindromic Repeats (CRISPR) nuclease (Barrangou, 2012). CRISPR is a microbial nuclease system involved in defence against invading phages and plasmids. CRISPR loci in microbial hosts contain a combination of CRISPR-associated (Cas) genes as well as non-coding RNA elements capable of programming the specificity of the CRISPR-mediated nucleic acid cleavage. Three types (I-III) of CRISPR systems have been identified across a wide range of bacterial hosts. One key feature of each CRISPR locus is the presence of an array of repetitive sequences (direct repeats) interspaced by short stretches of non-repetitive sequences (spacers). The non-coding CRISPR array is transcribed and cleaved within direct repeats into short crRNAs containing individual spacer sequences, which direct Cas nucleases to the target site (protospacer).

The Type II CRISPR carries out targeted DNA double-strand break in four sequential steps (for example, see Cong et al., 2013). First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Wastson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. The CRISPR system can also be used to generate single-stranded breaks in the genome. Thus the CRISPR system can be used for RNA guided (or RNA programmed) site specific genome editing.

In an embodiment, the nuclease is a RNA-guided engineered nuclease (RGEN). In an embodiment, the RGEN is from an archaeal genome or is a recombinant version thereof. In an embodiment, the RGEN is from a bacterial genome or is a recombinant version thereof. In an embodiment, the RGEN is from a Type I (CRISPR)-cas (CRISPR-associated) system. In an embodiment, the RGEN is from a Type II (CRISPR)-cas (CRISPR-associated) system. In an embodiment, the RGEN is from a Type III (CRISPR)-cas (CRISPR-associated) system. In an embodiment, the nuclease is a class I RGEN. In an embodiment, the nuclease is a class II RGEN. In an embodiment, the RGEN is a multi-component enzyme. In an embodiment, the RGEN is a single component enzyme. In an embodiment, the RGEN is CAS3. In an embodiment, the RGEN is CAS10. In an embodiment, the RGEN is CAS9. In an embodiment, the RGEN is Cpf1. In an embodiment, the RGEN is targeted by a single RNA or DNA. In an embodiment, the RGEN is targeted by more than one RNA and/or DNA. In an embodiment, the RGEN is a recombinant and/or a high fidelity nuclease.

In an embodiment, the programmable nuclease may be a transcription activator-like effector (TALE) nuclease (see, e.g., Zhang et al., 2011). TALEs are transcription factors from the plant pathogen *Xanthomonas* that can be readily engineered to bind new DNA targets. TALEs or truncated versions thereof may be linked to the catalytic domain of endonucleases such as Fok1 to create targeting endonuclease called TALE nucleases or TALENs.

In an embodiment, the programmable nuclease is a zinc-finger nuclease (ZFN). In one embodiment, each monomer of the ZFN comprises 3 or more zinc finger-based DNA binding domains, wherein each zinc finger-based DNA binding domain binds to a 3 bp subsite. In other embodiments, the ZFN is a chimeric protein comprising a zinc finger-based DNA binding domain operably linked to an independent nuclease. In one embodiment, the independent endonuclease is a FokI endonuclease. In one embodiment, the nuclease agent comprises a first ZFN and a second ZFN, wherein each of the first ZFN and the second ZFN is operably linked to a FokI nuclease, wherein the first and the second ZFN recognize two contiguous target DNA sequences in each strand of the target DNA sequence separated by about 6 bp to about 40 bp cleavage site or about a 5 bp to about 6 bp cleavage site, and wherein the FokI nucleases dimerize and make a double strand break (see, for example, US20060246567, US20080182332, US20020081614, US20030021776, WO/2002/057308, US20130123484, US20100291048 and WO/2011/017293).

In an embodiment, the programmable nuclease may be a DNA programmed argonaute (WO 14/189628). Prokaryotic and eukaryotic argonautes are enzymes involved in RNA interference pathways. An argonaute can bind and cleave a target nucleic acid by forming a complex with a designed nucleic acid-targeting acid.

Cleavage can introduce double stranded breaks in the target nucleic acid which can be repaired by non-homologous end joining machinery. A DNA "guided" or "programmed" argonaute can be directed to introducing double stranded DNA breaks in predetermined locations in DNA.

Traits

The methods of the invention will typically introduce the targeted germline genetic modification to alter a trait of an animal when compared to an isogenic animal lacking the genetic modification. Examples of traits which can be modified include, but are not limited to, disease resilience, muscle development (including muscle mass), skeletal development, allergenicity, sex and nutritional content.

In an embodiment, the animal is a mammal and the trait can be sex, age at puberty, reproductive potential, birth weight, longevity, weight of subject at a target timepoint, average weaning weight, rate of gain, days to a target weight, meat quality, feed efficiency, muscle content, muscle mass, fat content (leanness), disease resistance, disease susceptibility, feed intake, protein content, bone content, maintenance energy requirement, mature size, amino acid profile, fatty acid profile, stress susceptibility and response, digestive capacity, and myostatin activity, pattern of fat deposition, fertility, ovulation rate, optimal diet, conception rate or production of a therapeutic protein.

In another embodiment, the animal is an avian and the trait can be sex, egg production, feed efficiency, livability, meat yield, longevity, white meat yield, dark meat yield, disease resistance, disease susceptibility, optimal diet time to maturity, time to a target weight, weight at a target timepoint, average daily weight gain, meat quality, muscle content, muscle mass, fat content, feed intake, protein content, bone content, maintenance energy requirement, mature size, amino acid profile, fatty acid profile, stress susceptibility and response, digestive capacity, myostatin activity, pattern of fat deposition, fertility, ovulation rate, or conception rate. In one embodiment, the trait is resistance to *Salmonella* infection, ascites, and *listeria* infection. The egg characteristic can be allergen free, quality, size, shape, shelf-life, freshness, cholesterol content, color, biotin content, calcium content, shell quality, yolk color, lecithin content, number of yolks, yolk content, white content, vitamin content, vitamin D content, nutrient density, protein content, albumen content, protein quality, avidin content, fat content, saturated fat content, unsaturated fat content, interior egg quality, number of blood spots, air cell size, grade, a bloom characteristic, chalaza prevalence or appearance, ease of peeling, likelihood of being a restricted egg, *Salmonella* content.

In an embodiment, disease resilience is conferred by the transgene(s) encoding an antibody which binds a protein of a pathogen which causes the disease.

Examples of genes that can be targeted to modify disease resilience as a trait include virus receptors, such as Tva receptors for avian leukosis virus and other proteins such as natural resistance associated macrophage protein 1 (Nramp-1) (Zekarias et al., 2002), PrP, v-rel avian reticuloendotheliosis viral oncogene homolog A (RELA), beta-casein (βCN), lysostaphin (LSS), and lysozyme (LZ) (Laible et al., 2014).

In another example, a transgene encoding a pathogen inhibitory polynucleotide, and/or polypeptide encoded thereby, is inserted into the genome. The pathogen inhibitory polynucleotide may be, for example, a shRNA or an antisense polynucleotide. For instance, the transgene may encode multiple anti-avian influenza virus shRNAs as described in WO 2008/138072 and WO 2014/138792. In another example the inhibitory polynucleotide is a foot and mouth disease virus (FMD) shRNA or a prion protein (PrP) shRNA (Laible et al., 2014).

Examples of pathogens which can be targeted include viruses, bacteria, fungi, prozoans, nematodes and infectious proteins (prions). Examples of viruses include influenza virus, avian leukosis virus, blue tounge virus, Newcastle disease virus, chicken anaemia virus, infectious bursal disease virus, foot and mouth disease virus, porcine reproductive and respiratory syndrome virus, classical swine fever virus, bluetongue virus, akabane virus, infectious hematopoietic necrosis virus, viral haemorrhagic septicaemia virus, ross river virus and infectious pancreatic necrosis virus.

Examples of bacteria include *Bacillus anthracis, Leptospira, Anaplama ovis, Francisella tularensis, Borrelia recurrentis, Mycobacterium bovis, Escherichia coli, Mycoplasma gallisepticum, Myoplasma synoviae, Pasteurella multocida, Clostridium perfringens, Clostridium septicum, Clostridium colinum, Salmonella pullorum, Salmonella gallinarum, Salmonella typhimurium, Clostridium botulinum, Hemophilus gallinarum, Erysipelothrix insidiosa, Streptococcus pyogenes* and *Salmonella typhimurium*.

Examples of fungi include *Microsporum* spp, *Aspergillus* spp, *Cryptococcus* spp, *Chrysosporium* spp, *Trichophyton* spp, *Enterocytozoon* spp, *Fusarium* spp, *Malassezia* spp, *Microsporum* spp, *Mortierella* spp, *Phaeohyphomycosis* spp, *Candida* spp, and Histoplasmosis spp.

Examples of protozoans include *Coccidia* and *Histomanas meleagridis*.

Examples of nematodes include *Heterakis gallinae, Haemonchus contortus, Teladorsagia circumcincta, Trichostrongylus* spp and *Cooperia curticei*.

Examples of genes that can be targeted to modify muscle development as a trait in an avian include myostatin (MSTN), growth differentiation factor-8 (GDF-8), insulin-like growth factor 1 (IGF1), myogenic differentiation 1 (MyoD1), growth hormone (GH), growth hormone releasing factor (GRF), fibroblast growth factor 2 (FGF2), c-ski, interleukin-15 (IL-15) and fibroblast growth factor 5 (FGF5)

(U.S. Pat. No. 7,732,571, WO1991000287, WO1996037223, WO2007062000, U.S. Pat. No. 7,732, 571).

Examples of genes that can be targeted to modify skeletal development as a trait include ALX homeobox 1 (ALX1) and IGF1.

Examples of genes that can be targeted to modify alergenecity as a trait include ovomucoid (Gald1), ovalbumin, lysozyme and ovotransferrin, livetin, apovitillin, chicken serum albumin and YGP42 and phosvitin (Dhanapale et al., 2015).

Examples of genes that can be targeted to modify sex as a trait include doublesex and mab-3 related transcription factor 1 (DMRT1), altered form of PKC inhibitor/interacting protein (WPKCI), R-spondin, forkhead box L2 (FOXL2), FOX9, aromatase, anti-Müllerian hormone (AMH) and β-catenin.

Examples of genes that can be targeted to modify nutritional content and/or animal derived foods include casein, beta-lactoglobulin (BLG), alpha-lactalbumin (αLac), lactoferrin (LF), lysozyme (LZ), Fat-1, MSTN, GH, GRF, intermediate filament keratin (IF), fatty acid desaturation 2 (FAD2), stearoyl-CoA desaturase (SCD) and phytase (Laible et al., 2014).

In an embodiment, the transgene(s) may encode a therapeutic protein. In one example, the therapeutic protein is an antibody. Other examples of therapeutic proteins include the C1 inhibitor (Ruconest), antithrombin (ATryn), human serum albumin, alpha 1 antitrypsin, spider silk protein and human butyrylcholinesterase (Maksimenko et al., 2013).

EXAMPLES

Example 1—Targeted Germline Modification of Chickens

Materials and Methods
CRISPR, TALEN and Homologous Recombination Construct Evaluation Using GFP expressing PGC and fibroblast cell lines, TALENS and CRISPRs targeting GFP were pre-screened before use to identify effective guides and compare the efficiency of CRISPRs and TALENs.

In brief, chicken fibroblastic DF-1 cells stably expressing GFP were used to screen candidate CRISPR guide RNAs against GFP and DMRT1. DF-1 cells were grown in 5% $CO_2$ in Dulbecco's Modified Eagle's Medium (DMEM) containing 4.5 g/11 glucose, 1.5 g/l sodium bicarbonate, 10% fetal calf serum (FCS), 2 mM L-glutamine, supplemented with penicillin (100 U/ml) and streptomycin (100 µg/ml). Separate plasmids containing the Cas9 gene and the candidate guides were transfected into the GFP DF-1 cells using Lipofectamine 2000CD per manufactures instructions (Thermo Fisher).

A population of cells were transfected with plasmids containing guides targeting GFP, while another population was co-transfected with plasmids containing guides targeting both GFP and DMRT1. Cells were sorted for GFP expression on a BD FACSAria II flow cytometer (BD Biosciences, USA) equipped with 488 nm laser with 530/30 emission filter. DNA was isolated from the non-green population of cells per manufactures protocols (Qiagen) and PCR performed to amplify the either GFP or DMRT1, depending on the population of cells (Table 1).

PCR products were analysed on a 1.2% TAE agarose gel to determine the length of the amplicon. Gel band intensity was evaluated using GelQuant software (biochemlabsolutions.com). PCR products were cloned into the pGEM-Teasy plasmid vector and sent for sequencing (Micromon, Monash University, Melbourne, Australia).

CRISPR mRNA and Guide RNA Preparation.

Cas9 mRNA was purchased from Sigma-Aldrich. Guide RNAs were synthesized from plasmids per manufactures protocols using an Ambion T7MEGAshortscript™ Kit.

Animals

Roosters and hens were housed in floor pens with deep litter, with access to water and fed a commercial broiler diet ad libitum. They were kept in an 8/16 dark/light cycle. Eggs were collected daily and kept at 15° C. until being placed in an incubator at 37° C. All hatched chicks were co-housed in floor pens with heat lamps to provide warmth and fed an ad libitum diet of commercial chick feed.

RNA/Lipofectamine Incubation

CRISPR—30 µl of lipofectamine 2000 CD was combined with 200 µl of Opti-Pro media. Cas9 mRNA (8 µg) was combined with 100 µl of Opti-Pro media. For the GFP knockout two guide RNAs were used and 2 µg of each guide RNA (gRNA) (SEQ ID NOs 6 and 7) were combined with 100 µl of Opti-Pro media. Lipofectamine 2000 CD+Opti-Pro media solution (115 µl) was added separately to the mRNA and gRNA mixtures. Resulting mixtures were incubated at room temperature for 5 to 30 minutes.

For the DMRT1 knockout experiment half of the inseminations were done using 2 µg each of the two gRNAs (SEQ ID NO:16 and SEQ ID NO: 17), while the other half were done using 4 µg of guide 1 (SEQ ID NO:16) and 100 µM of a designed homology directed repair (HDR) oligo (SEQ ID NO: 18), with both combinations being prepared in 100 µl of Opti-Pro media.

After both the Cas9 mRNA and gRNA/oligos were diluted in Opti-Pro media 115 µl of the previously combined Lipofectamine 2000 CD+Opti-Pro media solution was added to both the Cas9 mRNA and gRNA/oligo mixtures. Resulting mixtures were incubated separately at room temperature for 5 to 30 minutes before being combined with the washed spermatozoa.

Semen Collection

All roosters were trained for semen collection prior to the start of the experiment using a modified method from Lake (1957). Briefly, a trained staff member would stroke the back of the bird and another staff member would collect the semen from the cloaca. For the GFP experiment semen from GFP and wildtype roosters were collected and pooled separately, while for the DMRT1 experiment all roosters were wildtype, thus all semen was pooled.

Sperm Preparation

Semen was harvested from hemizygous GFP roosters which produce 50% GFP spermatozoa as well as WT roosters which have no GFP in their spermatozoa. WT and GFP semen was treated separately. Spermatozoa were washed twice in Lakes extender by centrifugation at 300 g at 20° C. for 12 min. After washing the previously prepared mRNA/lipofectmine, gRNA/lipofectmine, mixtures diluted in Opti-Pro media were added to each sperm sample (sperm and PGE mixture) and incubated for 30 minutes at 4° C.

Inseminations

Artificial inseminations were carried out on hens using a syringe to deliver 100 µl to 150 µl of the sperm and PGE mixture into the *cloacae*. GFP sperm was inseminated into WT hens (GFP a WT 9) while WT sperm was inseminated into GFP hens (WT 5' GFP 9). Six consecutive artificial inseminations at 3 to 7 day intervals were carried out. For the DMRT1 experiment twelve consecutive inseminations were done using WT rooster and hens. Following insemination eggs (ovum) were collected and incubated at 15° C. for no more than 7 days, then incubated at 37° C. until screening.

Screening

Embryonic Day 2.5 Screening

A portion of eggs were screened at day 2.5 of embryonic development, ranging from Hamburger Hamilton stage 14 to 17 (Hamburger and Hamilton, 1951). Eggs were candled and a small window was made in fertile eggs to visually screen them for GFP expression. Pictures of the developing embryos were taken on a Leica MZ95 microscope using a Leica DFC 290 digital camera, and then embryos were collected for DNA analysis. Blood samples were collected from 2 GFP expressing embryos and from all non-GFP expressing (WT phenotype) embryos. Eggs were resealed and placed back into the incubator. At day 7 of embryonic development all samples that were PCR positive (PCR+) for the GFP gene were used for cyto-spotting of the embryonic gonads.

Embryonic Day 7 Screening

A portion of eggs from the GFP experiment were screened at day 7 of embryonic development. A small window was made in fertile eggs to visually screen them for GFP expression. Brightfield and fluorescent photographs of the whole embryos and embryonic gonads were taken using a Leica DMLB fluorescent microscope with a Leica DC 300F digital camera. Tissue samples were collected from a selection of GFP expressing embryos and from all non-GFP expressing (WT phenotype) embryos.

Embryonic Day 11 Screening

A portion of eggs from both the GFP and DMRT1 experiments were screened at day 11 of embryonic development. All eggs was first candled to determine fertility and a window was made into fertile eggs. For the DMRT1 experiment embryos were removed from the eggs and a small portion of the developing wing or leg was taken for DNA extraction and PCR analysis of sex (SEQ ID NO: 14 and SEQ ID NO: 15). The gonads were photographed using a Leica MZ95 microscope using a Leica DFC 290 digital camera and gonadal samples taken. For the GFP experiment after a small window was made in the fertile eggs to visually screen them for GFP expression, tissue samples for microscopy and DNA analysis were collected from a selection of GFP expressing embryos and from all non-GFP expressing (WT phenotype) embryos. Bright-field and fluorescent photographs of collected tissues were taken using a Leica DMLB fluorescent microscope with a Leica DC 300F digital camera using the 4× objective, with some samples undergoing further investigation using the 20× and 40× objective.

7 Day Old Chick Screening

A portion of eggs from the GFP experiment were hatched and chicks were visually screened for GFP expression. All WT phenotype chicks and 2 GFP expressing chicks were kept and at 7 days of age were euthanized, necropsied, and gonad, muscle, intestinal, and skin tissue samples were collected. Bright-field and fluorescent photographs of collected tissues were taken using a Leica DMLB fluorescent microscope with a Leica DC 300F digital camera at 4× magnification, with some samples undergoing further investigation at 20× and 40× magnification.

PCR from Blood and Tissue Samples

Genomic DNA was isolated from blood and tissue samples per manufactures protocols (Qiagen, DNeasy Blood & Tissue Kit (cat no: 69504)). PCR primers were designed for GFP 5' and 3' of the two CRISPR guide RNAs (Fwd 5'-AGCCTCTGCTAACCATGTTC-3' (SEQ ID NO:8), Rev 5'-CGTCCATGCCGTGAGTGATC-3' (SEQ ID NO:9)) as well as for chicken β-actin (Fwd 5'-CAACACAGTGCTGTCTGGTGG-3' (SEQ ID NO:10), Rev 5'-ATCGTACTCCTGCTTGCTGAT-3' (SEQ ID NO:11)) and for the two DMRT1 guides (FWD 5'AGCAAGCCCAGGAAGAGGAG 3' (SEQ ID NO:12), REV 5'GTTCCAGTGTAGTGCAGGAG 3' (SEQ ID NO:13)). PCR were performed with using GoTaq® Green Master Mix (Promega), 100 ng of genomic DNA and primers at a final concentration of 0.5 µM. Cycling conditions were an initial denaturing step at 94° C. for 2 minutes followed by 30 cycles of denaturing at 94° C. for 30 seconds, annealing at 60° C. for 30 seconds, and extension at 72° C. for 1 minute. PCRs were stored at 4° C. until being run on a 1.2% agarose gel (FIGS. 1 A and B).

Tissue Microscopy

Tissue samples collected from day 7 and day 11 embryos were used for microscopy. Tissues from day 11 embryos were photographed under an inverted microscope (Leica) at 4× magnification under both bright-field and florescent conditions using a GFP filter (FIG. 2).

Sequencing

PCR products were cloned into the PGem plasmid and sequenced (Micromon, Melbourne Australia). Sequences were aligned to control sequences from GFP expressing chickens and the original plasmid that was used to generate the GFP chicken line using Clone Manager 9 Professional Edition (FIG. 2). While for the DMRT1 study control samples were obtained from embryos resulting from a control insemination with no gene editing components. As additional controls in the GFP experiment the GFP gene was sequenced from the grandparental rooster, and the mosaic founder rooster from the GFP expressing line, while for the DMRT1 project the DMRT1 gene was sequenced in fertile chickens. In addition, the DMRT1 gene was sequenced in a selection of embryos and chicks from the GFP experiment.

Results

CRISPR Guide Identification

The in vitro experiments identified 2 CRISPR guides that effectively cleaved the GFP gene (SEQ ID NO:6 and SEQ ID NO:7) and 2 guides approximately 165 base pairs away from each other that that cleaved the DMRT1 gene were identified (SEQ ID NO: 12 and SEQ ID NO:13). For the GFP experiment approximately 4% of the DF-1 cells transfected with both guides appeared to no longer express GFP (unpublished results). Analysis of the gel band intensity of GFP PCR products from the pool of cells appearing to no longer express GFP indicated that of those cells 85.5% still retained a full length transcript, while 14.5% had a truncated transcript about 240 base pairs shorter than the full length transcript (FIG. 1C). For the DMRT1 DF-1 experiment PCR results from the pool of co-selected cells indicate that approximately 90.7% of cells retained a full length transcript, while 9.3% had a truncated transcript approximately 165 base pairs shorter than the full length transcript (FIG. 1C).

Sequencing Results from DF-1 Cells

From the GFP cell culture experiment samples of both full length and truncated transcript were sequenced. Of the 8 full length transcripts 3 had single base pair mutations within a range of 100 base pairs upstream or downstream from the CRISPR sites (FIG. 6). The remaining 5 samples had no mutations and likely came from cells with low GFP expression which where mischaracterized during flow cytometry. The truncated transcripts were missing the DNA region between the two CRISPR sites, indicating that both CRISPRs were able to cut and the piece of DNA in between was deleted.

For the DMRT1 experiment full length and truncated transcripts were also sent for sequencing. Of the 7 full length transcripts sent all contained mutations. Six samples had mutations in the first CRISPR site, and of those six, one sample also had a single base pair mutation in the second CRISPR site, which was the only mutation seen in the second CRISPR site. Four of those six samples with mutations in the first CRISPR site also had additional single base pair mutations between 5 to 150 base pairs upstream and downstream of either of the CRISPR sites. The one sample which did not have a mutation in the first CRISPR site did have a single base pair mutation about 35 base pairs upstream of the first CRISPR site (FIG. 7). The truncated transcripts were missing the DNA region between the two CRISPR sites, indicating that both CRISPRs were able to cut and the region of DNA in between was deleted.

GFP

Grandparental, Parental, and Cohort Sequencing

Sequencing from the GFP chicken line mosaic founder rooster, the grandparental rooster, and the parental roosters as well as GFP expressing embryos and birds generated during the experiment revealed no mutations in the GFP gene (Table 1 and FIG. 8).

GFP♂ GFP ♀ Group

GFP♂ GFP ♀ inseminations yielded 111 eggs, all of which were screened at embryonic day 7 (ED 7). Of these eggs 18 (16%) were viable at ED 7, and of those 18, 13 had the GFP phenotype and 5 had the WT phenotype (Table 2). One of the WT phenotype embryos was PCR positive for the GFP gene. Microscopy revealed the embryo had a consistent WT phenotype and sequencing revealed DNA mutations in the GFP region (Table 1, FIG. 3 and FIG. 4).

GFP♂ WT♀ Group

GFP♂ WT♀ inseminations yielded a total of 159 eggs. Of those, 19 were screened at ED 7 and 12 (63%) were found to be viable, of which 8 had the GFP phenotype and 4 had the WT phenotype (Table 2). None of the WT phenotype embryos were PCR positive for the GFP gene. On embryonic day 11 (ED 11) 80 eggs were screened, 32 (40%) of which were viable at ED 11, and of those 32, 11 expressed GFP and 21 had the WT phenotype. PCR revealed that of the 21 WT phenotype embryos 4 were PCR positive for the GFP gene (Table 2).

Florescence microscopy revealed that of the 4 PCR positive ED 11 embryos 3 were confirmed to have a consistent WT phenotype (FIG. 3 and FIG. 4), while 1 was mosaic (data not shown), and sequencing revealed various DNA mutations in the GFP region of all 4 of these embryos, however both mutated and wildtype sequence were found in the mosaic embryo (Table 2) (FIG. 4). The remaining 60 eggs were allowed to hatch and of these 11 were viable at hatch and 5 were significantly developed but failed to hatch (FTH). Of the 16 chicks/FTH embryos visual screening revealed that 8 expressed GFP and 8 had the WT phenotype. Of the 8 with the WT phenotype, 2 were PCR positive for GFP (one chick and one FTH embryo) and fluorescence microscopy revealed both had a consistent WT phenotype (FIG. 3 and FIG. 4) while sequencing revealed various DNA mutations in the GFP region (Table 1).

TABLE 1

List of mutations found in each sample

| Group | Bird number | Mutation location |
|---|---|---|
| GFP: CRISPR1: +44 to +67, 2: +284 to +307 † | | |
| 7 GFP parent roosters from semen collection | 1-7 | No mutations |
| Grandparental rooster | — | No mutations |
| GFP line founder rooster | — | No mutations |
| Embryonic day 11 | 1-30+ | No mutations |
| Hatch | 214+ | No mutations |
| Embryonic day 7 | 1-1 | T→C (+529) |
| | | A→G (+606) |
| Embryonic day 11 | 1-10 | A→G (−10) |
| | | A→G (+1) |
| | | G→A (+462) |
| Embryonic day 11 | 1-13 | Insertion of C (+635) |
| Embryonic day 11 | 1-15* | A→G (−10) |
| | | A→G (+1) |
| | | T→G (+24) |
| Embryonic day 11 | 1-23 | A→G (−10) |
| | | A→G (+1) |
| | | T→G (+24) |
| Embryonic day 11 | 1-52 | Insertion of C (+465) |
| Hatch | 203 | A→G (+438) |
| | | Insertion of C (+544, +604) |
| | | Insertion of A (+645, +669) |
| | | Insertion of G (+660) |
| Hatch | 211 | A→G (+64, +324) |
| | | T→C (+67) |
| | | Insertion of A (+422) |
| Hatch | 212 | T→C (+484) |
| | | A→G (+629) |
| FTH Embryo | D2 | A→G (+384) |
| DMRT1: CRISPR 1: +154 to +177, 2: +318 to +341 † | | |
| 7 Embryos from control insemination | CI 12 through 18+ | No mutations |
| 3 fertile chickens | — | No mutations |
| 4 samples from GFP study | 1-10, 1-13, 1-15, 1-23 | No mutations in DMRT1 |
| Embryonic day 2.5 CRISPR1 & HDR | 6-8 | T→C (+98) |
| | | Insertion of TG (+99) |
| Embryonic day 2.5 CRISPR1 & HDR | 6-10 | C→T (+96, +103) |
| | | T→C (+98) |
| | | G→C (+99) |
| | | C→G (+101) |
| | | Insertion TCCTT (+106) |
| | | Insertion A (+126) |
| | | Insertion T (+130) |
| Embryonic day 2.5 CRISPR1 & HDR | 6-68 | T→G (+177) |

+Indicates positive control

*Sample 1-15 was chimeric and also contained sequences of non-mutated GFP.

† CRISPR and mutation locations for GFP were calculated from the ATG start site, CRISPR and mutation locations for DMRT1 were calculated from the beginning of DMRT1 exon 2.

TABLE 2

Fertility, phenotypic, and genotypic results

GFP

| Age | Treatment group | Total eggs | Total viable/ FTH* | Phenotype: GFP/WT Genotype: GFP/WT | | GFP genotype samples with WT phenotype (% of GFP genotype group with KO) |
|---|---|---|---|---|---|---|
| ED 7 | GFP ♂ WT ♀ | 19 | 12 | P 8:4 | G 8:4 | 0 (0%) |
|  | GFP ♂ GFP ♀ | 111 | 18 | P 13:5 | G 14:4 | 1 (7.1%) |
| ED 11 | GFP ♂ WT ♀ | 80 | 32 | P 11:21 | G 15:17 | 4 (26.6%) |
|  | WT ♂ GFP ♀ | 63 | 21 | P 10:11 | G 11:10 | 1 (9.1%) |
| Hatch | GFP ♂ WT ♀ | 60 | 11/5 | P 8:8 | G 10:6 | 2 (20%) |
| D7 | WT ♂ GFP ♀ | 62 | 10/8 | P 10:8 | G 12:6 | 2 (16.6%) |

DMRT1

| Embryo stage | Treatment group | Total eggs | Total viable embryos/NV† | Phenotype: F/M/? Genotype: F/M | | Numbers of embryos with mutations (% of total group) |
|---|---|---|---|---|---|---|
| ED 2.5 | CRISPR 1 & 2 | 93 | 61/3 | — | | 0 (0%) |
|  | CRISPR 1 & HDR | 92 | 70/1 | — | | 3 (4.3%) |
| ED 11 | CRISPR 1 & 2 | 156 | 58/14 | P 20:35:3 | G 29:29 | 0 (0%) |
|  | CRISPR 1 & HDR | 194 | 68/6 | P 33:30:6 | G 37:32 | 0 (0%) |

*FTH indicates embryos that were significantly developed but failed to hatch.
†NV indicates non-viable embryos.

A total of 143 day 11 eggs were screened with 53 found to have live embryos. 32 live embryos resulted from GFP ♂ WT ♀ inseminations and 21 resulted from WT ♂ GFP ♀ inseminations (Table 2). Upon visual screening of the GFP ♂ WT ♀ derived embryos 11 expressed GFP and 21 had the WT phenotype, while for the WT ♂ GFP ♀ embryos 10 expressed GFP and 11 had the WT phenotype. PCR revealed that of the 21 WT phenotype embryos from the GFP ♂ WT ♀ group 5 were PCR positive for the GFP gene. From the WT ♂ GFP ♀ group of the 11 WT phenotype embryos 1 was PCR positive for the GFP gene (FIG. 1).

Florescence microscopy was performed on PCR positive embryos to confirm the WT phenotype. Of the 6 PCR positive embryos 5 were confirmed to have the WT phenotype (FIG. 2A), while 1 was chimeric (FIG. 2B). Sequencing of the region of the genome containing the GFP gene was performed on PCR positive embryos with WT phenotype or chimeric phenotype as well as a GFP phenotype animal as a positive control. Sequencing revealed mutations in the start codon as well as mutations +24, −5, −10, and −15 (FIG. 3).

Sequencing from fertile flock chickens and progeny from the GFP experiment Sequencing from embryos generated in control inseminations and sequencing from fertile flock chickens revealed no mutations in the DMRT1 gene. Sequencing from a selection of embryos which did show mutations in GFP also showed no mutations in DMRT1 (Table 1 and FIG. 9).

DMRT1 gRNAs 1 and 2

Inseminations including DMRT1 gRNAs 1 and 2 yielded a total of 249 eggs. Of these 93 eggs were screened at embryonic day 2.5 (ED 2.5) and 61 (66%) were classified as viable embryos, 3 (3%) as non-viable, and 29 (31%) as infertile. DNA samples were prepared from all viable and early dead embryos, yielding 64 samples. After PCR analysis, 6 samples from the ED 2.5 group were sent for sequencing but none were found to have mutations in the DMRT1 region. The remaining 156 eggs were screened at ED 11 and 58 (37%) were classified as viable embryos, 14 (9%) as non-viable and 84 (54%) as infertile. DNA samples were prepared and phenotypic and genotypic evaluation of sex was carried out on all viable embryos. Phenotypic assessment determined that there were 20 female (34.5%), 35 (60.5%) male, and 3 (5%) unclassified embryos, while genotypic assessment revealed that there were 29 female (50%) and 29 (50%) male embryos meaning multiple female embryos were misclassified as male, and the 3 unclassified embryos were all female. Following PCR analysis, 16 samples from the ED 11 group were sent for sequencing with no samples found to have mutations in the DMRT1 region.

DMRT1 gRNA 1 and the HDR Oligo

Inseminations including gRNA 1 and the HDR oligo yielded a total of 286 eggs. Of these 92 of these were screened at ED 2.5 with 70 (76%) classified as viable embryos, 1 (1%) as non-viable, 19 (21%) as infertile, and 2 (2%) eggs were unable to be classified due to operator error while opening the eggs (Table 2). It was only possible to prepare DNA samples from the viable embryos, yielding 70 samples. After PCR analysis. 15 samples from the ED 2.5 group were sent for sequencing and 3 were found to have mutations in the DMRT1 region, however none were found to have integrated the HDR oligo (Table 1 and FIG. 1C). Genotypic assessment showed that 2 of the edited embryos were male and 1 was female. There were no obvious phenotypic differences in the embryos containing mutations in DMRT1 (FIG. 5), however one of the embryos with mutations in DMRT1 was damaged during collection so no microscopic image is available. The remaining 194 eggs were screened at ED 11. Of those screened 68 (35%) were classified as viable embryos, 6 (3%) were classified as non-viable, and 120 (62%) were classified as infertile (Table 2). DNA samples were prepared and phenotypic and genotypic evaluation of sex was carried out on all viable embryos and 1 non-viable embryo, yielding 69 samples. Of those 33 (48%) were phenotypically classified as females, 30 (43%) were phenotypically classified as males, and 6 (9%) were unclassified, 5 due to operator error during sample collection. Genotypic assessment revealed that 37 (54%) of the embryos were female and 32 (46%) were male. The 1 true unclassified embryo was genetically female, while of the 5 operator error embryos 2 were male and 3 were female. Following PCR analysis 3 samples from the ED 11 group were sent for sequencing and none were found to have mutations in the DMRT1 region.

Discussion

Work to test the sperm transfection assisted gene editing method (the STAGE method) was carried out in chickens by the present inventors and employed a Lipofectamine transfection system to deliver CRISPR/Cas9 tools into the sperm cytosol. In the GFP experiment the STAGE method proved to be effective with an average efficiency of 14%. Some of the edits observed were found between 50 to 200 base pairs away from the CRISPR sites. Multiple single base pair changes and multi-base pair insertions were also observed.

When using STAGE to target DMRT1, mutations were seen in one of the 4 groups, which was day 2.5 embryos targeted with a single DMRT1 CRISPR guide (guide 1; SEQ ID NO:16) and HDR oligo. In terms of the type of mutations seen the results for DMRT1 were similar to those seen in the GFP experiment, with some mutations occurring up to 60 base pairs upstream of the CRISPR site. These results are similar to results seen in cells in culture targeted with the DMRT1 CRISPR guides, which also exhibited single base mutations and multi-base deletions outside of the CRISPR sites. However, most samples also contained edits within the DMRT1 CRISPR guide 1 site. It is noted that is it possible that knocking out DMRT1 function is lethal and DMRT1 edited embryos may have died early on in embryogenesis. Since initial screening of the day 11 embryos involved candling the eggs to view the developing vasculature it is possible that embryos that died prior to development of a robust vascular system may have been incorrectly characterized as infertile and not sampled. Fertility data suggests that at least some embryos that died early in embryogenesis in the day 11 group may have been miscategorised in this way as the average fertility for eggs screened on day 2.5 was 72% (with 70% classified as viable and 2% as early dead) while for day 11 screenings the average fertility was only 42% (with 36% characterized as viable and 6% as dead). Only seeing mutations with the delivery of 1 DMRT1 CRISPR guide (guide 1; SEQ ID NO:16) could indicate that a certain threshold amount of guide is needed for STAGE. Additionally, data from cell culture experiments revealed that 86% of full length sequenced transcripts from cells delivered both guides had edits in the DMRT1 guide 1 CRISPR site, while only 14% had edits in the guide 2 (SEQ ID NO: 17) CRISPR site. This indicates that the DMRT1 guide 1 was generally more efficient, which could be another reason mutations where only seen when delivering a higher dose of DMRT1 guide 1 as opposed to a lower dose of both guides. Methods of screening for effective CRISPR guides and determining the concentration/dose of guide required would be known by persons skilled in the art.

It is noted that there was a clear phenotypic screening process for GFP knockout, which was not possible with DMRT1. The initial screening process for DMRT1 involved evaluating the size of PCR products, however the mutations seen in the DMRT1 gene consisted of small insertions and deletions, and it is possible that some embryos containing mutations were not identified via PCR and thus not sequenced.

Since the STAGE process places the CRISPR components in such close proximity to the paternal genome the GFP experiment was designed to test if STAGE could induce mutations from both the maternal and paternal germline. From the GFP experiment 6 of the editing events were in paternal alleles while 3 were in maternal alleles. This shows that STAGE is capable of inducing mutations in both paternal and maternal alleles. It should be also noted that the embryo with mosaicism throughout (1-15) had a paternal GFP allele and the chicken with partial mosaicism in the gonad (212) had a maternal GFP allele, indicating that when using STAGE mosaicism can be seen in alleles from either parent. Overall, STAGE is a novel and effective method for generating gene edited chickens in one generation, and has the potential to be applied to other bird species.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

This application claims priority from Australian Provisional Application No. 2015903164 entitled "method for producing an animal comprising a germline genetic modification" filed on 7 Aug. 2015. The entire contents of that application are hereby incorporated by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

The steps, features, integers, compositions and/or compounds disclosed herein or indicated in the specification of this application individually or collectively, and any and all combinations of two or more of said steps or features.

REFERENCES

Ball et al. (2008) Equine Vet J 40:76-82.
Barrangou (2012) Nature Biotechnology 30:836-838.
Collares et al. (2011) J Biosci 36:613-620.
Cong et al. (2013) Science 339:819-823.
Dhanapala et al. (2015) Mol Immunol 66:375-385.
Gagne et al. (1991) Mol Reprod and Develop. 29:6-15.
García-Vázquez et al. (2009) Theriogenology 72:506-518.
Haensler and Szoka (1993) Bioconjugate Chem 4:372-379.
Hamburger and Hamilton (1951) J Morphol 88:49-92.
Laible et al (2014) Biotech Jour 10:109-120.
Lake (1957) Journal of Ag Sci 49:120-126.
Lavitrano et al. (1989) Cell 57: 717-723.
Maksimenko et al. (2013) Acta Naturae 5:33-26
Nakanishi and Iritani (1993) Mol Reprod Dev 36:258-261.
Pereyra-Bonnet et al. (2011) J Reprod Dev 57:188-196.
Shemesh et al. (2000) Mol Reprod Dev 56:306-308.
Tang et al. (1996) Bioconjugate Chem 7:703-714.
Zekarias et al. (2002) Vet Res 33:109-125.
Zhang et al. (2011) Nature Biotechnology 29:149-153.

The invention claimed is:

1. A method for producing a non-human animal comprising a targeted germline modification, the method comprising:
   (i) administering a composition comprising a monovalent or polyvalent cationic lipid transfection agent, a RNA-guided engineered programmable nuclease (RGEN) protein and a RGEN RNA guide to sperm in vitro;
   (ii) following (i) fertilizing an ovum with the sperm,
   (iii) generating an animal from the fertilized ovum,
   (iv) screening the animal obtained from step (iii) for the targeted germline genetic modification,
   wherein the RGEN protein introduces the genetic modification into the maternal derived DNA of the fertilized ovum, and wherein all cells of the animal comprise the targeted germline genetic modification.

2. The method of claim 1, wherein the transfection agent comprises a monovalent cationic lipid selected from one or more of DOTMA (N-[1-(2.3-dioleoyloxy)-propyl]-N,N,N-trimethyl ammonium chloride), DOTAP (1,2-bis(oleoyloxy)-3-3-(trimethylammonium)propane), DMRIE (1,2-dimyristyloxypropyl-3-dimethyl-hydroxy ethyl ammonium bromide) and DDAB (dimethyl dioctadecyl ammonium bromide).

3. The method of claim 1, wherein the transfection agent comprises a polyvalent cationic lipid selected from one or more of DOSPA (2,3-dioleyloxy-N-[2(sperminecarboxamido)ethyl]-N,N-dimethyl-1-propanaminium trifluoroacetate), DOSPER (1,3-dioleoyloxy-2-(6carboxy spermyl)-propyl-amid, TMTPS (tetramethyltetrapalmitoylspermine), TMTOS (tetramethyltetraoleylspermine), TMTLS (tetramethyltetralaurylspermine), TMTMS (tetramethyltetramyristylspermine) and TMDOS (tetramethyldioleylspermine).

4. The method according to of claim 1, wherein the genetic modification is a deletion, substitution or an insertion.

5. The method of claim 4, wherein the genetic modification is an insertion of a transgene and the composition of step (i) comprises an exogenous nucleic acid comprising the transgene.

6. The method of claim 1, wherein step (ii) comprises artificially inseminating the sperm into a female animal.

7. The method of claim 1, wherein the animal is an avian.

8. The method of claim 7, wherein the avian is selected from the group consisting of a chicken, duck, turkey, goose, bantam and quail.

9. A method for producing a genetically modified animal, the method comprising:
   (i) crossing a first animal produced by the method of claim 1 with a second animal of the same species, and
   (ii) selecting progeny comprising the targeted germline genetic modification.

10. The method of claim 9 which comprises selecting progeny which are homozygous for the targeted germline genetic modification.

11. The method of claim 10, wherein the first and second animal are heterozygous for the targeted germline genetic modification.

12. The method of claim 1, wherein at least 10% of the animals produced using the method comprise the targeted germline genetic modification.

* * * * *

SEQUENCE LISTING

<160> NUMBER OF SEQ ID NOS: 67

<210> SEQ ID NO 1
<211> LENGTH: 839
<212> TYPE: DNA
<213> ORGANISM: Artificial Sequence
<220> FEATURE:
<223> OTHER INFORMATION: Region of inverted_pT2 plasmid used to generate GFP birds

<400> SEQUENCE: 1

| | | | | | |
|---|---|---|---|---|---|
| tgaccggcgg | ctctagagcc | tctgctaacc | atgttcatgc | cttcttcttt | ttcctacagc | 60 |
| tcctgggcaa | cgtgctggtt | attgtgctgt | ctcatcattt | tggcaaagaa | ttgtaccacc | 120 |
| atggtgagca | agggcgagga | gctgttcacc | ggggtggtgc | ccatcctggt | cgagctggac | 180 |
| ggcgacgtaa | acggccacaa | gttcagcgtg | tccggcgagg | gcgagggcga | tgccacctac | 240 |
| ggcaagctga | ccctgaagtt | catctgcacc | accggcaagc | tgcccgtgcc | ctggcccaca | 300 |
| ctagtgacca | ccttcgctta | cggcgtgcag | tgcttcagcc | gctaccccga | ccacatgaag | 360 |
| cagcacgact | tcttcaagtc | cgccatgccc | gaaggctacg | tccaggagcg | caccatcttc | 420 |
| ttcaaggacg | acggcaacta | caagacccgc | gccgaggtga | agttcgaggg | cgacaccctg | 480 |
| gtgaaccgca | tcgagctgaa | gggcatcgac | ttcaaggagg | acggcaacat | cctggggcac | 540 |
| aagctggagt | acaacttcaa | cagccacaac | gtatacatca | tggccgacaa | gcagaagaac | 600 |
| ggcatcaagg | tgaacttcaa | gatccgccac | aacatcgagg | acggcagcgt | gcagctcgcc | 660 |
| gaccactacc | agcagaacac | ccccatcggc | gacggccccg | tgctgctgcc | cgacaaccac | 720 |
| tacctgagca | cccagtccgc | cctgagcaaa | gaccccaacg | agaagcgcga | tcacatggtc | 780 |
| ctgctggagt | tcgtgaccgc | cgccgggatc | actcacggca | tggacgagct | gtacaagta | 839 |

<210> SEQ ID NO 2
<211> LENGTH: 763
<212> TYPE: DNA
<213> ORGANISM: Artificial Sequence
<220> FEATURE:
<223> OTHER INFORMATION: Region corresponding to SEQ ID NO:1 from I_30 which is a GFP expressing embryo

<400> SEQUENCE: 2

| | | | | | |
|---|---|---|---|---|---|
| ggtcctgggc | acgtgctggt | tattgtgctg | tctcatcatt | ttggcaaaga | attgtaccac | 60 |
| catggtgagc | aagggcgagg | agctgttcac | cggggtggtg | cccatcctgg | tcgagctgga | 120 |
| cggcgacgta | aacggccaca | agttcagcgt | gtccggcgag | ggcgagggcg | atgccaccta | 180 |
| cggcaagctg | accctgaagt | tcatctgcac | caccggcaag | ctgcccgtgc | cctggcccac | 240 |
| actagtgacc | accttcgctt | acggcgtgca | gtgcttcagc | cgctaccccg | accacatgaa | 300 |
| gcagcacgac | ttcttcaagt | ccgccatgcc | cgaaggctac | gtccaggagc | gcaccatctt | 360 |
| cttcaaggac | gacggcaact | acaagacccg | cgccgaggtg | aagttcgagg | gcgacaccct | 420 |
| ggtgaaccgc | atcgagctga | agggcatcga | cttcaaggag | gacggcaaca | tcctggggca | 480 |
| caagctggag | tacaacttca | acagccacaa | cgtatacatc | atggccgaca | agcagaagaa | 540 |
| cggcatcaag | gtgaacttca | agatccgcca | caacatcgag | gacggcagcg | tgcagctcgc | 600 |
| cgaccactac | cagcagaaca | ccccccatcgg | cgacggcccc | gtgctgctgc | ccgacaacca | 660 |
| ctacctgagc | acccagtccg | ccctgagcaa | agaccccaac | gagaagcgcg | atcacatggt | 720 |
| cctgctggag | ttcgtgaccg | ccgccgggat | cactcccggc | atg | | 763 |

```
<210> SEQ ID NO 3
<211> LENGTH: 758
<212> TYPE: DNA
<213> ORGANISM: Artificial Sequence
<220> FEATURE:
<223> OTHER INFORMATION: Region corresponding to SEQ ID NO:1 from I_10
      which is a GFP PCR positive embryo that has a WT phenotype

<400> SEQUENCE: 3
cgtgctggtt attgtgctgt ctcatcattt tggcagagaa ttgtaccacc gtggtgagca     60
agggcgagga gctgttcacc ggggtggtgc ccatcctggt cgagctggac ggcgacgtaa    120
acggccacaa gttcagcgtg tccggcgagg gcgagggcga tgccacctac ggcaagctga    180
ccctgaagtt catctgcacc accggcaagc tgcccgtgcc ctggcccaca ctagtgacca    240
ccttcgctta cggcgtgcag tgcttcagcc gctaccccga ccacatgaag cagcacgact    300
tcttcaagtc cgccatgccc gaaggctacg tccaggagcg caccatcttc ttcaaggacg    360
acggcaacta caagacccgc gccgaggtga agttcgaggg cgacaccctg gtgaaccgca    420
tcgagctgaa gggcatcgac ttcaaggagg acggcaacat cctggggcac aagctggagt    480
acaacttcaa cagccacaac gtatacatca tggccgacaa gcagaagaac ggcatcaagg    540
tgaacttcaa gatccgccac aacatcgagg acggcagcgt gcagctcgcc gaccactacc    600
agcagaacac ccccatcggc gacggccccg tgctgctgcc cgacaaccac tacctgagca    660
cccagtccgc cctgagcaaa gaccccaacg agaagcgcga tcacatggtc ctgctggagt    720
tcgtgaccgc cgccgggatc actcacgggc atggacga                            758

<210> SEQ ID NO 4
<211> LENGTH: 766
<212> TYPE: DNA
<213> ORGANISM: Artificial Sequence
<220> FEATURE:
<223> OTHER INFORMATION: Region corresponding to SEQ ID NO:1 from I_15
      which is a GFP PCR positive embryo that has a WT phenotype

<400> SEQUENCE: 4
tcgtgggcac gtgctggtta ttgtgctgtc tcatcatttt ggcagagaat tgtaccaccg     60
tggtgagcaa gggcgaggag ctggtcaccg ggtggtgcc catcctggtc gagctggacg    120
gcgacgtaaa cggccacaag ttcagcgtgt ccggcgaggg cgagggcgat gccacctacg    180
gcaagctgac cctgaagttc atctgcacca ccggcaagct gcccgtgccc tggcccacac    240
tagtgaccac cttcgcttac ggcgtgcagt gcttcagccg ctaccccgac cacatgaagc    300
agcacgactt cttcaagtcc gccatgcccg aaggctacgt ccaggagcgc accatcttct    360
tcaaggacga cggcaactac aagacccgcg ccgaggtgaa gttcgagggc gacaccctgg    420
tgaaccgcat cgagctgaag ggcatcgact tcaaggagga cggcaacatc ctggggcaca    480
agctggagta caacttcaac agccacaacg tatacatcat ggccgacaag cagaagaacg    540
gcatcaaggt gaacttcaag atccgccaca acatcgagga cggcagcgtg cagctcgccg    600
accactacca gcagaacacc cccatcggcg acggccccgt gctgctgccc gacaaccact    660
acctgagcac ccagtccgcc ctgagcaaag accccaacga gaagcgcgat cacatggtcc    720
tgctggagtt cgtgaccgcc gccgggatca ctcacggcat ggacga                   766

<210> SEQ ID NO 5
<211> LENGTH: 748
<212> TYPE: DNA
<213> ORGANISM: Artificial Sequence
<220> FEATURE:
```

<223> OTHER INFORMATION: Region corresponding to SEQ ID NO:1 from I_23
      which is a GFP PCR positive embryo that has a WT phenotype

<400> SEQUENCE: 5
cgtgcgggtt attgggctgt ctcatcgttt tggcagagaa gtgtaccacc gtggtgagca      60
agggcgagga gctggtcacc ggggtggtgc ccatcctggt cgagctggac ggcgacgtaa     120
acggccacaa gttcagcgtg tccggcgagg gcgagggcga tgccacctac ggcaagctga     180
ccctgaagtt catctgcacc accggcaagc tgcccgtgcc ctggcccaca ctagtgacca     240
ccttcgctta cggcgtgcag tgcttcagcc gctaccccga ccacatgaag cagcacgact     300
tcttcaagtc cgccatgccc gaaggctacg tccaggagcg caccatcttc ttcaaggacg     360
acggcaacta caagacccgc gccgaggtga agttcgaggg cgacaccctg gtgaaccgca     420
tcgagctgaa gggcatcgac ttcaaggagg acggcaacat cctggggcac aagctggagt     480
acaacttcaa cagccacaac gtatacatca tggccgacaa gcagaagaac ggcatcaagg     540
tgaacttcaa gatccgccac aacatcgagg acggcagcgt gcagctcgcc gaccactacc     600
agcagaacac ccccatcggc gacggccccg tgctgctgcc cgacaaccac tacctgagca     660
cccagtccgc cctgagcaaa gaccccaacg agaagcgcga tcacatggtc ctgctggagt     720
tcgtgaccgc cgccgggatc actcacgg                                        748

<210> SEQ ID NO 6
<211> LENGTH: 23
<212> TYPE: RNA
<213> ORGANISM: Artificial Sequence
<220> FEATURE:
<223> OTHER INFORMATION: Guide RNA sg-GFP-1

<400> SEQUENCE: 6
gcagcggcag gucgagcugg ucc                                              23

<210> SEQ ID NO 7
<211> LENGTH: 23
<212> TYPE: RNA
<213> ORGANISM: Artificial Sequence
<220> FEATURE:
<223> OTHER INFORMATION: Guide RNA sg-GFP-2

<400> SEQUENCE: 7
ccucgcgugg uagaagaagu ucc                                              23

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 8
agcctctgct aaccatgttc                                                  20

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 9
cgtccatgcc gtgagtgatc                                                  20

```
<210> SEQ ID NO 10
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 10
caacacagtg ctgtctggtg g                                              21

<210> SEQ ID NO 11
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 11
atcgtactcc tgcttgctga t                                              21

<210> SEQ ID NO 12
<211> LENGTH: 20
<212> TYPE: DNA
<213> ORGANISM: Artificial Sequence
<220> FEATURE:
<223> OTHER INFORMATION: DMRT1 PCT Primer FWD

<400> SEQUENCE: 12
agcaagccca ggaagaggag                                                20

<210> SEQ ID NO 13
<211> LENGTH: 20
<212> TYPE: DNA
<213> ORGANISM: Artificial Sequence
<220> FEATURE:
<223> OTHER INFORMATION: DMRT1 PCR Primer REV

<400> SEQUENCE: 13
gttccagtgt agtgcaggag                                                20

<210> SEQ ID NO 14
<211> LENGTH: 22
<212> TYPE: DNA
<213> ORGANISM: Artificial Sequence
<220> FEATURE:
<223> OTHER INFORMATION: Sex test PCR Primer FWD

<400> SEQUENCE: 14
cccaaatata acacgcttca ct                                             22

<210> SEQ ID NO 15
<211> LENGTH: 23
<212> TYPE: DNA
<213> ORGANISM: Artificial Sequence
<220> FEATURE:
<223> OTHER INFORMATION: Sex test PCR Primer REV

<400> SEQUENCE: 15
gaaatgaatt attttctggc gac                                            23

<210> SEQ ID NO 16
<211> LENGTH: 23
<212> TYPE: RNA
<213> ORGANISM: Artificial Sequence
<220> FEATURE:
<223> OTHER INFORMATION: DMRT1 CRISPR guide 1
```

-continued

```
<400> SEQUENCE: 16
cgucgucgcu cgcguggugg ucc                                           23

<210> SEQ ID NO 17
<211> LENGTH: 23
<212> TYPE: RNA
<213> ORGANISM: Artificial Sequence
<220> FEATURE:
<223> OTHER INFORMATION: DMRT1 CRISPR guide 2

<400> SEQUENCE: 17
cuuuguacug ccugauugug acc                                           23

<210> SEQ ID NO 18
<211> LENGTH: 99
<212> TYPE: DNA
<213> ORGANISM: Artificial Sequence
<220> FEATURE:
<223> OTHER INFORMATION: DMRT1 HDR oligo

<400> SEQUENCE: 18
ctgctcactc cacgagcacg gtggcagcag cagcagcgag cgctagtcta gactagtcag   60
tgccagtgag gggcccactg ctccttgctg cccaggcag                          99

<210> SEQ ID NO 19
<211> LENGTH: 719
<212> TYPE: DNA
<213> ORGANISM: Gallus gallus

<400> SEQUENCE: 19
attgtgctgt ctcatcattt tggcaaagaa ttgtaccacc atggtgagca agggcgagga   60
gctgttcacc ggggtggtgc ccatcctggt cgagctggac ggcgacgtaa acggccacaa  120
gttcagcgtg tccggcgagg gcgagggcga tgccacctac ggcaagctga ccctgaagtt  180
catctgcacc accggcaagc tgcccgtgcc ctggcccaca ctagtgacca ccttcgctta  240
cggcgtgcag tgcttcagcc gctaccccga ccacatgaag cagcacgact tcttcaagtc  300
cgccatgccc gaaggctacg tccaggagcg caccatcttc ttcaaggacg acggcaacta  360
caagacccgc gccgaggtga agttcgaggg cgacaccctg gtgaaccgca tcgagctgaa  420
gggcatcgac ttcaaggagg acggcaacat cctggggcac aagctggagt acaacttcaa  480
cagccacaac gtatacatca tggccgacaa gcagaagaac ggcatcaagg tgaacttcaa  540
gatccgccac aacatcgagg acggcagcgt gcagctcgcc gaccactacc agcagaacac  600
ccccatcggc gacggccccg tgctgctgcc cgacaaccac tacctgagca cccagtccgc  660
cctgagcaaa gaccccaacg agaagcgcga tcacatggtc ctgctggagt tcgtgaccg   719

<210> SEQ ID NO 20
<211> LENGTH: 719
<212> TYPE: DNA
<213> ORGANISM: Gallus gallus

<400> SEQUENCE: 20
attgtgctgt ctcatcattt tggcagagaa ttgtaccacc gtggtgagca agggcgagga   60
gctgttcacc ggggtggtgc ccatcctggt cgagctggac ggcgacgtaa acggccacaa  120
gttcagcgtg tccggcgagg gcgagggcga tgccacctac ggcaagctga ccctgaagtt  180
catctgcacc accggcaagc tgcccgtgcc ctggcccaca ctagtgacca ccttcgctta  240
```

| | |
|---|---|
| cggcgtgcag tgcttcagcc gctaccccga ccacatgaag cagcacgact tcttcaagtc | 300 |
| cgccatgccc gaaggctacg tccaggagcg caccatcttc ttcaaggacg acggcaacta | 360 |
| caagacccgc gccgaggtga agttcgaggg cgacaccctg gtgaaccgca tcgagctgaa | 420 |
| gggcatcgac ttcaaggagg acggcaacat cctggggcac aagctggagt acaacttcaa | 480 |
| cagccacaac gtatacatca tggccgacaa gcagaagaac ggcatcaagg tgaacttcaa | 540 |
| gatccgccac aacatcgagg acggcagcgt gcagctcgcc gaccactacc agcagaacac | 600 |
| ccccatcggc gacggccccg tgctgctgcc cgacaaccac tacctgagca cccagtccgc | 660 |
| cctgagcaaa gaccccaacg agaagcgcga tcacatggtc ctgctggagt tcgtgaccg | 719 |

<210> SEQ ID NO 21
<211> LENGTH: 719
<212> TYPE: DNA
<213> ORGANISM: Gallus gallus

<400> SEQUENCE: 21

| | |
|---|---|
| attgtgctgt ctcatcattt tggcaaagaa ttgtaccacc atggtgagca agggcgagga | 60 |
| gctgttcacc ggggtggtgc ccatcctggt cgagctggac ggcgacgtaa acggccacaa | 120 |
| gttcagcgtg tccggcgagg gcgagggcga tgccacctac ggcaagctga ccctgaagtt | 180 |
| catctgcacc accggcaagc tgcccgtgcc ctggcccaca ctagtgacca ccttcgctta | 240 |
| cggcgtgcag tgcttcagcc gctaccccga ccacatgaag cagcacgact tcttcaagtc | 300 |
| cgccatgccc gaaggctacg tccaggagcg caccatcttc ttcaaggacg acggcaacta | 360 |
| caagacccgc gccgaggtga agttcgaggg cgacaccctg gtgaaccgca tcgagctgaa | 420 |
| gggcatcgac ttcaaggagg acggcaacat cctggggcac aagctggagt acaacttcaa | 480 |
| cagccacaac gtatacatca tggccgacaa gcagaagaac ggcatcaagg tgaacttcaa | 540 |
| gatccgccac aacatcgagg acggcagcgt gcagctcgcc gaccactacc agcagaacac | 600 |
| ccccatcggc gacggccccg tgctgctgcc cgacaaccac tacctgggca cccagtccgc | 660 |
| cctgagcaaa gaccccaacg agaagcgcga tcacatggtc ctgctggagt tcgtgaccg | 719 |

<210> SEQ ID NO 22
<211> LENGTH: 719
<212> TYPE: DNA
<213> ORGANISM: Gallus gallus

<400> SEQUENCE: 22

| | |
|---|---|
| attgtgctgt ctcatcattt tggcagagaa ttgtaccacc gtggtgagca agggcgagga | 60 |
| gctggtcacc ggggtggtgc ccatcctggt cgagctggac ggcgacgtaa acggccacaa | 120 |
| gttcagcgtg tccggcgagg gcgagggcga tgccacctac ggcaagctga ccctgaagtt | 180 |
| catctgcacc accggcaagc tgcccgtgcc ctggcccaca ctagtgacca ccttcgctta | 240 |
| cggcgtgcag tgcttcagcc gctaccccga ccacatgaag cagcacgact tcttcaagtc | 300 |
| cgccatgccc gaaggctacg tccaggagcg caccatcttc ttcaaggacg acggcaacta | 360 |
| caagacccgc gccgaggtga agttcgaggg cgacaccctg gtgaaccgca tcgagctgaa | 420 |
| gggcatcgac ttcaaggagg acggcaacat cctggggcac aagctggagt acaacttcaa | 480 |
| cagccacaac gtatacatca tggccgacaa gcagaagaac ggcatcaagg tgaacttcaa | 540 |
| gatccgccac aacatcgagg acggcagcgt gcagctcgcc gaccactacc agcagaacac | 600 |
| ccccatcggc gacggccccg tgctgctgcc cgacaaccac tacctgagca cccagtccgc | 660 |
| cctgagcaaa gaccccaacg agaagcgcga tcacatggtc ctgctggagt tcgtgaccg | 719 |

<210> SEQ ID NO 23
<211> LENGTH: 720
<212> TYPE: DNA
<213> ORGANISM: Gallus gallus

<400> SEQUENCE: 23

| | |
|---|---|
| attgtgctgt ctcatcattt tggcaaagaa ttgtaccacc atggtgagca agggcgagga | 60 |
| gctgttcacc ggggtggtgc ccatcctggt cgagctggac ggcggcgtaa acggccacaa | 120 |
| gttcagcgtg tccggcgagg gcgagggcga tgccacctac ggcaagctga ccctgaagtt | 180 |
| catctgcacc accggcaagc tgcccgtgcc ctggcccaca ctagtgacca ccttcgctta | 240 |
| cggcgtgcag tgcttcagcc gctaccccga ccacatgaag cagcacgact tcttcaagtc | 300 |
| cgccatgccc gaaggctacg tccaggagcg caccatcttc ttcaaggacg acggcaacta | 360 |
| caaggcccgc gccgaggtga agttcgaggg cgacaccctg gtgaaccgca tcgagctgaa | 420 |
| gggcatcgac ttcaaggagg acggcaacat cctggggcac aaagctggag tacaacttca | 480 |
| acagccacaa cgtatacatc atggccgaca agcagaagaa cggcatcaag gtgaacttca | 540 |
| agatccgcca caacatcgag gacggcagcg tgcagctcgc cgaccactac cagcagaaca | 600 |
| cccccatcgg cgacggcccc gtgctgctgc ccgacaacca ctacctgagc acccagtccg | 660 |
| ccctgagcaa agaccccaac gagaagcgcg atcacatggt cctgctggag ttcgtgaccg | 720 |

<210> SEQ ID NO 24
<211> LENGTH: 137
<212> TYPE: DNA
<213> ORGANISM: Gallus gallus

<400> SEQUENCE: 24

| | |
|---|---|
| cagcagcagc agctcctgtc tcctgcagga cagcagcagc cctgctcact ccacgagcac | 60 |
| ggtggcagca gcagcagcga gcgcaccacc aggtcagtgc cagtgagggg cccactgctc | 120 |
| cttgctgccc aggcagc | 137 |

<210> SEQ ID NO 25
<211> LENGTH: 139
<212> TYPE: DNA
<213> ORGANISM: Gallus gallus

<400> SEQUENCE: 25

| | |
|---|---|
| cagcagcagc agctccctgg tctcctgcag gacagcagca gccctgctca ctccacgagc | 60 |
| acggtggcag cagcagcagc gagcgcacca ccaggtcagt gccagtgagg ggcccactgc | 120 |
| tccttgctgc ccaggcagc | 139 |

<210> SEQ ID NO 26
<211> LENGTH: 144
<212> TYPE: DNA
<213> ORGANISM: Gallus gallus

<400> SEQUENCE: 26

| | |
|---|---|
| cagcagcagc agcttccctg ttcttccttg caggacagca gcagccctag cttcactcca | 60 |
| cgagcacggt ggcagcagca gcagcgagcg caccaccagg tcagtgccag tgaggggccc | 120 |
| actgctcctt gctgcccagg cagc | 144 |

<210> SEQ ID NO 27
<211> LENGTH: 137
<212> TYPE: DNA

<213> ORGANISM: Gallus gallus

<400> SEQUENCE: 27

| | |
|---|---|
| cagcagcagc agctcctgtc tcctgcagga cagcagcagc cctgctcact ccacgagcac | 60 |
| ggtggcagca gcagcagcga gcgcaccacc agggcagtgc cagtgagggg cccactgctc | 120 |
| cttgctgccc aggcagc | 137 |

<210> SEQ ID NO 28
<211> LENGTH: 560
<212> TYPE: DNA
<213> ORGANISM: Gallus gallus

<400> SEQUENCE: 28

| | |
|---|---|
| tgtctcatca ttttggcaaa gaattgtacc accatggtga gcaagggcga ggagctgttc | 60 |
| accggggtgg tgcccatcct ggtcgagctg gacggcgacg taaacggcca caagttcagc | 120 |
| gtgtccggcg agggcgaggg cgatgccacc tacggcaagc tgaccctgaa gttcatctgc | 180 |
| accaccggca agctgcccgt gccctggccc acactagtga ccaccttcgc ttacggcgtg | 240 |
| cagtgcttca gccgctaccc cgaccacatg aagcagcacg acttcttcaa gtccgccatg | 300 |
| cccgaaggct acgtccagga gcgcaccatc ttcttcaagg acgacggcaa ctacaagacc | 360 |
| cgcgccgagg tgaagttcga gggcgacacc ctggtgaacc gcatcgagct gaagggcatc | 420 |
| gacttcaagg aggacggcaa catcctgggg cacaagctgg agtacaactt caacagccac | 480 |
| aacgtataca tcatggccga caagcagaag aacggcatca aggtgaactt caagatccgc | 540 |
| cacaacatcg aggacggcag | 560 |

<210> SEQ ID NO 29
<211> LENGTH: 560
<212> TYPE: DNA
<213> ORGANISM: Gallus gallus

<400> SEQUENCE: 29

| | |
|---|---|
| tgtctcatca ttttggcaaa gaattgtacc accatggtga gcaagggcga ggagctgttc | 60 |
| accggggtgg tgcccatcct ggtcgagctg gacggcgacg taaacggcca caagttcagc | 120 |
| gtgtccggcg agggcgaggg cgatgccacc tacggcaagc tgaccctgaa gttcatctgc | 180 |
| accaccggca agctgcccgt gccctggccc acactagtga ccaccttcgc ttacggcgtg | 240 |
| cagtgcttca gccgctaccc cgaccacatg aagcagcacg acttcttcaa gtccgccatg | 300 |
| cccgaaggct acgtccagga gcgcaccatc ttcttcaagg acgacggcaa ctacaagacc | 360 |
| cgcgccgagg tgaagttcga gggcgacacc ctggtgaacc gcatcgagct gaagggcatc | 420 |
| gacttcaagg aggacggcaa catcctgggg cacaagctgg agtacaactt caacagccac | 480 |
| aacgtataca tcatggccga caagcagaag aacggcatca aggtgaactt caagatccgc | 540 |
| cacaacatcg aggacggcag | 560 |

<210> SEQ ID NO 30
<211> LENGTH: 560
<212> TYPE: DNA
<213> ORGANISM: Gallus gallus

<400> SEQUENCE: 30

| | |
|---|---|
| tgtctcatca ttttggcaaa gaattgtacc accatggtga gcaagggcga ggagctgttc | 60 |
| accggggtgg tgcccatcct ggtcgagctg gacggcgacg taaacggcca caagttcagc | 120 |
| gtgtccggcg agggcgaggg cgatgccacc tacggcaagc tgaccctgaa gttcatctgc | 180 |

```
accaccggca agctgcccgt gccctggccc acactagtga ccaccttcgc ttacggcgtg    240
cagtgcttca gccgctaccc cgaccacatg aagcagcacg acttcttcaa gtccgccatg    300
cccgaaggct acgtccagga gcgcaccatc ttcttcaagg acgacggcaa ctacaagacc    360
cgcgccgagg tgaagttcga gggcgacacc ccggtgaacc gcatcgagct gaagggcatc    420
gacttcaagg aggacggcaa catcctgggg cacaagctgg agtacaactt caacagccac    480
aacgtataca tcatggccga caagcagaag aacggcatca aggtgaactt caagatccgc    540
cacaacatcg aggacggcag                                                560

<210> SEQ ID NO 31
<211> LENGTH: 560
<212> TYPE: DNA
<213> ORGANISM: Gallus gallus

<400> SEQUENCE: 31
tgtctcatca ttttggcaaa gaattgtacc accatggtga gcaagggcga ggagctgttc     60
accggggtgg tgcccatcct ggtcgagctg gacggcgacg taaacggcca caagttcagc    120
gtgtccggcg agggcgaggg cgatgccacc tacggcaagc tgaccctgaa gttcatctgc    180
accaccggca agctgcccgt gccctggccc acactagtga ccaccttcgc ttacggcgtg    240
cagtgcttca gccgctaccc cgaccacatg aagcagcacg acttcttcaa gtccgccatg    300
cccgaaggct acgtccagga gcgcaccatc ttcttcaagg acgacggcaa ctacaagacc    360
cgcgccgagg tgaagttcga gggcgacacc ctggtgaacc gcatcgagct gaagggcatc    420
gacttcaagg aggacggcaa catcctgggg cacaagctgg agtacaactt caacagccac    480
aacgtataca tcatggccga caagcagaag aacggcatca aggtgaactt caagatccgc    540
cacaacatcg aggacggcag                                                560

<210> SEQ ID NO 32
<211> LENGTH: 560
<212> TYPE: DNA
<213> ORGANISM: Gallus gallus

<400> SEQUENCE: 32
tgtctcatca ttttggcaaa gaattgtacc gccatggtga gcaagggcga ggagctgttc     60
accggggtgg tgcccatcct ggtcgagctg gacggcgacg taaacggcca caagttcagc    120
gtgtccggcg agggcgaggg cgatgccacc tacggcaagc tgaccctgaa gttcatctgc    180
accaccggca agctgcccgt gccctggccc acactagtga ccaccttcgc ttacggcgtg    240
cagtgcttca gccgctaccc cgaccacatg aagcagcacg acttcttcaa gtccgccatg    300
cccgaaggct acgtccagga gcgcaccatc ttcttcaagg acgacggcaa ctacaagacc    360
cgcgccgagg tgaagttcga gggcgacacc ctggtgaacc gcatcgagct gaagggcatc    420
gacttcaagg aggacggcaa catcctgggg cacaagctgg agtacaactt caacagccac    480
aacgtataca tcatggccga caagcagaag aacggcatca aggtgaactt caagatccgc    540
cacaacatcg aggacggcag                                                560

<210> SEQ ID NO 33
<211> LENGTH: 560
<212> TYPE: DNA
<213> ORGANISM: Gallus gallus
```

<400> SEQUENCE: 33

```
tgtctcatca tttggcaaa gaattgtacc accatggtga gcaagggcga ggagctgttc    60
accggggtgg tgcccatcct ggtcgagctg gacggcgacg taaacggcca caagttcagc   120
gtgtccggcg agggcgaggg cgatgccacc tacggcaagc tgaccctgaa gttcatctgc   180
accaccggca agctgcccgt gccctggccc acactagtga ccaccttcgc ttacggcgtg   240
cagtgcttca gccgctaccc cgaccacatg aagcagcacg acttcttcaa gtccgccatg   300
cccgaaggct acgtccagga gcgcaccatc ttcttcaagg acgacggcaa ctacaagacc   360
cgcgccgagg tgaagttcga gggcgacacc ctggtgaacc gcatcgagct gaagggcatc   420
gacttcaagg aggacggcaa catcctgggg cacaagctgg agtacaactt caacagccac   480
aacgtataca tcatggccga caagcagaag aacggcatca aggtgaactt caagatccgc   540
cacaacatcg aggacggcag                                              560
```

<210> SEQ ID NO 34
<211> LENGTH: 560
<212> TYPE: DNA
<213> ORGANISM: Gallus gallus

<400> SEQUENCE: 34

```
tgtctcatca tttggcaaa gaattgtacc accatggtga gcaagggcga ggagctgttc    60
accggggtgg tgcccatcct ggtcgagctg gacggcgacg taaacggcca caagttcagc   120
gtgtccggcg agggcgaggg cgatgccacc tacggcaagc tgaccctgaa gttcatctgc   180
accaccggca agctgcccgt gccctggccc acactagtga ccaccttcgc ttacggcgtg   240
cagtgcttca gccgctaccc cgaccacatg aagcagcacg acttcttcaa gtccgccatg   300
cccgaaggct gcgtccagga gcgcaccatc ttcttcaagg acgacggcaa ctacaagacc   360
cgcgccgagg tgaagttcga gggcgacacc ctggtgaacc gcatcgagct gaagggcatc   420
gacttcaagg aggacggcaa catcctgggg cacaagctgg agtacaactt caacagccac   480
aacgtataca tcatggccga caagcagaag aacggcatca aggtgaactt caagatccgc   540
cacaacatcg aggacggcag                                              560
```

<210> SEQ ID NO 35
<211> LENGTH: 560
<212> TYPE: DNA
<213> ORGANISM: Gallus gallus

<400> SEQUENCE: 35

```
tgtctcatca tttggcaaa gaattgtacc accatggtga gcaagggcga ggagctgttc    60
accggggtgg tgcccatcct ggtcgagctg gacggcgacg taaacggcca caagttcagc   120
gtgtccggcg agggcgaggg cgatgccacc tacggcaagc tgaccctgaa gttcatctgc   180
accaccggca agctgcccgt gccctggccc acactagtga ccaccttcgc ttacggcgtg   240
cagtgcttca gccgctaccc cgaccacatg aagcagcacg acttcttcaa gtccgccatg   300
cccgaaggct acgtccagga gcgcaccatc ttcttcaagg acgacggcaa ctacaagacc   360
cgcgccgagg tgaagttcga gggcgacacc ctggtgaacc gcatcgagct gaagggcatc   420
gacttcaagg aggacggcaa catcctgggg cacaagctgg agtacaactt caacagccac   480
aacgtataca tcatggccga caagcagaag aacggcatca aggtgaactt caagatccgc   540
cacaacatcg aggacggcag                                              560
```

<210> SEQ ID NO 36
<211> LENGTH: 560
<212> TYPE: DNA
<213> ORGANISM: Gallus gallus

<400> SEQUENCE: 36

```
tgtctcatca tttttggcaaa gaattgtacc accatggtga gcaagggcga ggagctgttc    60
accggggtgg tgcccatcct ggtcgagctg gacggcgacg taaacggcca caagttcagc   120
gtgtccggcg agggcgaggg cgatgccacc tacggcaagc tgaccctgaa gttcatctgc   180
accaccggca agctgcccgt gccctggccc acactagtga ccaccttcgc ttacggcgtg   240
cagtgcttca gccgctaccc cgaccacatg aagcagcacg acttcttcaa gtccgccatg   300
cccgaaggct acgtccagga gcgcaccatc ttcttcaagg acgacggcaa ctacaagacc   360
cgcgccgagg tgaagttcga gggcgacacc ctggtgaacc gcatcgagct gaagggcatc   420
gacttcaagg aggacggcaa catcctgggg cacaagctgg agtacaactt caacagccac   480
aacgtataca tcatggccga caagcagaag aacggcatca aggtgaactt caagatccgc   540
cacaacatcg aggacggcag                                                560
```

<210> SEQ ID NO 37
<211> LENGTH: 400
<212> TYPE: DNA
<213> ORGANISM: Gallus gallus

<400> SEQUENCE: 37

```
tgcccctgag ccagttgtca agaagagcag cagcagcagc tcctgtctcc tgcaggacag    60
cagcagccct gctcactcca cgagcacggt ggcagcagca gcagcgagcg caccaccagg   120
tcagtgccag tgaggggccc actgctcctt gctgcccagg cagcactgct gctccatatg   180
ctgcctgcgg ccacagggct ggagtcccct ctccagcaac tgcatcatgc tgctggcgca   240
gctagtgaga gggaggaaac cagtgttagt ccgtcatgtt tcattatttt cacttgaaaa   300
ataaaattag ctctgaatag accagcactg cattgaattt catgggttgt gctgcaagta   360
gtgattcaca aggagttttt ctcctttcta ccaaaacaca                          400
```

<210> SEQ ID NO 38
<211> LENGTH: 397
<212> TYPE: DNA
<213> ORGANISM: Gallus gallus

<400> SEQUENCE: 38

```
tgcccctgag ccagttgtca agaagagcag cagcagcagc tcctgtctcc tgcaggacag    60
cagcagccct gctcactcca cgagcacggt ggcagcagca gcagcgagcg caccaggtca   120
gtgccagtga ggggcccact gctccttgct gcccaggcag cactgctgct ccatatgctg   180
cctgcggcca cagggctgga gtcccctctc agcaactgc atcatgctgc tggcgcagct   240
agtgagaggg aggaaaccag tgttagtccg tcatgtttca ttattttcac ttgagaaata   300
aaattagctc tgaatagacc agcactgcat tgaatttcat gggttgtgct gcaagtagtg   360
attcacaagg agttttctc ctttctacca aaacaca                             397
```

<210> SEQ ID NO 39
<211> LENGTH: 396
<212> TYPE: DNA
<213> ORGANISM: Gallus gallus

```
<400> SEQUENCE: 39
tgcccctgag ccagttgtca agaagagcag cagcagcagc tcctgtctcc tgcaggacag      60
cagcagccct gctcactcca cgagcacggt ggcagcagca gcgagcgcac gccaggtcag     120
tgccagtgag gggcccactg ctccttgctg cccaggcagc actgctgctc catatgctgc     180
ctgcggccac agggctggag tcccctctcc agcaactgca tcatgctgct ggcgcagcta     240
gtgagaggga ggaaaccagt gttagtccgt catgtttcat tattttcact tgaaaaataa     300
aattagctct gaatagacca gcactgcatt gaatttcatg ggttgtgctg caagtagtga     360
ttcacaagga gtttttctcc tttctaccaa aacaca                               396

<210> SEQ ID NO 40
<211> LENGTH: 399
<212> TYPE: DNA
<213> ORGANISM: Gallus gallus

<400> SEQUENCE: 40
tgcccctgag ccagttgtca agaagagcag cagcagcagc tcctgtctcc tgcaggacag      60
cagcagccct gctcactcca cgagcacggt ggcagcagca gcagcgagcg cacaccaggt     120
cagtgccagt gaggggccca ctgctccttg ctgcccaggc agcactgctg ctccatatgc     180
tgcctgcggc cacagggctg gagtcccctc tccagcaact gcatcatgct gctggcgcag     240
ctagtgagag ggaggaaacc agtgttagtc cgtcatgttt cattattttc acttgaaaaa     300
taaaattagc tctgaataga ccagcactgc attgaatttc atgggttgtg ctgcaagtag     360
tgattcacaa ggagtttttc tcctttctac aaaacaca                             399

<210> SEQ ID NO 41
<211> LENGTH: 400
<212> TYPE: DNA
<213> ORGANISM: Gallus gallus

<400> SEQUENCE: 41
tgcccctgag ccagttgtca agaagagcag cagcagcagc tcctgtctcc tgcaggacag      60
cagcggccct gctcactcca cgagcacggt ggcagcagca gcagcgagcg caccaccagg     120
tcagtgccag tgaggggccc actgctcctt gctgcccagg cagcactgct gctccatatg     180
ctgcctgcgg ccacagggct ggagtcccct ctccagcaac tgcatcatgc tgctggcgca     240
gctagtgaga gggaggaaac cagtgttagt ccgtcatgtt tcattatttt cacttgaaaa     300
ataaaattag ctctgaatag accagcactg cattgaattt catgggttgt gctgcaagta     360
gtgattcaca aggagttttt ctcctttcta ccaaaacaca                            400

<210> SEQ ID NO 42
<211> LENGTH: 399
<212> TYPE: DNA
<213> ORGANISM: Gallus gallus

<400> SEQUENCE: 42
tgcccctgag ccagttgtca agaagagcag cagcagcagc tcctgtctcc tgcaggacag      60
cagcagccct gctcactcca cgagcacggt ggcagcagca gcagcgagcg cacaccaggt     120
cagtgccagt gaggggccca ctgctccttg ctgcccaggc agcactgctg ctccatatgc     180
tgcctgcggc cacagggctg gagtcccctc tccagcaact gcatcatgct gctggcgcag     240
ctagtgagag ggaggaaacc agtgttagtc cgtcatgttt cattattttc acttgaaaaa     300
```

```
taaaattagc tctgaataga ccagcactgc attgaatttc atgggttgtg ctgcaagtag    360
tgattcacaa ggagtttttc tcctttctac caaaacaca                          399

<210> SEQ ID NO 43
<211> LENGTH: 399
<212> TYPE: DNA
<213> ORGANISM: Gallus gallus

<400> SEQUENCE: 43
tgcccctgag ccagttgtca agaagagcag cagcagcagc tcctgtctcc tgcaggacag    60
cagcagccct gctcgctcca cgagcacggt ggcagcagca gcagcgagcg cacaccaggt   120
cagtgccagt gaggggccca ctgcttcttg ctgcccaggc agcactgctg ctccatatgc   180
tgcctgcggc cacagggctg gagtcccctc tccagcaact gcatcatgct gctggcgcag   240
ctagtgagag ggaggaaacc agcgttagtc cgtcatgttt cattattttc acttgaaaaa   300
taaaattagc tctgaataga ccagcactgc attgaatttc atgggttgtg ctgcaagtag   360
tgattcacaa ggagtttttc tcctttctac caaaacaca                          399

<210> SEQ ID NO 44
<211> LENGTH: 393
<212> TYPE: DNA
<213> ORGANISM: Gallus gallus

<400> SEQUENCE: 44
tgcccctgag ccagttgtca agaagagcag cagcagcagc tcctgtctcc tgcaggacag    60
cagcagccct gctcactcca cgagcacggt ggcagcagca gcagcgagcc aggtcagtgc   120
cagtgagggg cccactgctc cttgctgccc aggcagcact gctgctccat atgctgcctg   180
cggccacagg gctggagtcc cctctccagc aactgcatca tgctgctggc gcagctagtg   240
agagggagga aaccagtgtt agtccgtcat gtttcattat tttcacttga aaataaaat   300 tagctctgaa tagaccagca ctgcattgaa tttcatgggt tgtgctgcaa gtagtgattc   360
acaaggagtt tttctccttt ctaccagagc aca                                393

<210> SEQ ID NO 45
<211> LENGTH: 630
<212> TYPE: DNA
<213> ORGANISM: Gallus gallus

<400> SEQUENCE: 45
ttattgtgct gtctcatcat tttggcaaag aattgtacca ccatggtgag caagggcgag    60
gagctgttca ccggggtggt gcccatcctg gtcgagctgg acggcgacgt aaacggccac   120
aagttcagcg tgtccggcga gggcgagggc gatgccacct acggcaagct gaccctgaag   180
ttcatctgca ccaccggcaa gctgcccgtg ccctggccca cactagtgac caccttcgct   240
tacggcgtgc agtgcttcag ccgctacccc gaccacatga agcagcacga cttcttcaag   300
tccgccatgc ccgaaggcta cgtccaggag cgcaccatct tcttcaagga cgacggcaac   360
tacaagaccc gcgccgaggt gaagttcgag ggcgacaccc tggtgaaccg catcgagctg   420
aagggcatcg acttcaagga ggacggcaac atcctgggc acaagctgga gtacaacttc   480
aacagccaca acgtatacat catggccgac aagcagaaga cggcatcaa ggtgaacttc   540 aagatccgcc acaacatcga ggacggcagc gtgcagctcg ccgaccacta ccagcagaac   600 accccatcg cgacggccc cgtgctgctg                                     630
```

<210> SEQ ID NO 46
<211> LENGTH: 630
<212> TYPE: DNA
<213> ORGANISM: Gallus gallus

<400> SEQUENCE: 46

```
ttattgtgct gtctcatcat tttggcaaag aattgtacca ccatggtgag caagggcgag      60
gagctgttca ccggggtggt gcccatcctg gtcgagctgg acggcgacgt aaacggccac     120
aagttcagcg tgtccggcga gggcgagggc gatgccacct acggcaagct gaccctgaag     180
ttcatctgca ccaccggcaa gctgcccgtg ccctggccca cactagtgac caccttcgct     240
tacggcgtgc agtgcttcag ccgctacccc gaccacatga agcagcacga cttcttcaag     300
tccgccatgc ccgaaggcta cgtccaggag cgcaccatct tcttcaagga cgacggcaac     360
tacaagaccc gcgccgaggt gaagttcgag ggcgacaccc tggtgaaccg catcgagctg     420
aagggcatcg acttcaagga ggacggcaac atcctggggc acaagctgga gtacaacttc     480
aacagccaca cgtatacat catggccgac aagcagaaga cggcatcaa ggtgaacttc       540
aagatccgcc acaacatcga ggacggcagc gtgcagctcg ccgaccacta ccagcagaac     600
accccccatcg gcgacggccc cgtgctgctg                                     630
```

<210> SEQ ID NO 47
<211> LENGTH: 630
<212> TYPE: DNA
<213> ORGANISM: Gallus gallus

<400> SEQUENCE: 47

```
ttattgtgct gtctcatcat tttggcaaag aattgtacca ccatggtgag caagggcgag      60
gagctgttca ccggggtggt gcccatcctg gtcgagctgg acggcgacgt aaacggccac     120
aagttcagcg tgtccggcga gggcgagggc gatgccacct acggcaagct gaccctgaag     180
ttcatctgca ccaccggcaa gctgcccgtg ccctggccca cactagtgac caccttcgct     240
tacggcgtgc agtgcttcag ccgctacccc gaccacatga agcagcacga cttcttcaag     300
tccgccatgc ccgaaggcta cgtccaggag cgcaccatct tcttcaagga cgacggcaac     360
tacaagaccc gcgccgaggt gaagttcgag ggcgacaccc tggtgaaccg catcgagctg     420
aagggcatcg acttcaagga ggacggcaac atcctggggc acaagctgga gtacaacttc     480
aacagccaca cgtatacat catggccgac aagcagaaga cggcatcaa ggtgaacttc       540
aagatccgcc acaacatcga ggacggcagc gtgcagctcg ccgaccacta ccagcagaac     600
accccccatcg gcgacggccc cgtgctgctg                                     630
```

<210> SEQ ID NO 48
<211> LENGTH: 630
<212> TYPE: DNA
<213> ORGANISM: Gallus gallus

<400> SEQUENCE: 48

```
ttattgtgct gtctcatcat tttggcaaag aattgtacca ccatggtgag caagggcgag      60
gagctgttca ccggggtggt gcccatcctg gtcgagctgg acggcgacgt aaacggccac     120
aagttcagcg tgtccggcga gggcgagggc gatgccacct acggcaagct gaccctgaag     180
ttcatctgca ccaccggcaa gctgcccgtg ccctggccca cactagtgac caccttcgct     240
tacggcgtgc agtgcttcag ccgctacccc gaccacatga agcagcacga cttcttcaag     300
tccgccatgc ccgaaggcta cgtccaggag cgcaccatct tcttcaagga cgacggcaac     360
```

```
tacaagaccc gcgccgaggt gaagttcgag ggcgacaccc tggtgaaccg catcgagctg      420
aagggcatcg acttcaagga ggacggcaac atcctggggc acaagctgga gtacaacttc      480
aacagccaca acgtatacat catggccgac aagcagaaga acggcatcaa ggtgaacttc      540
aagatccgcc acaacatcga ggacggcagc gtgcagctcg ccgaccacta ccagcagaac      600 accccccatcg gcgacggccc cgtgctgctg                                      630

<210> SEQ ID NO 49
<211> LENGTH: 630
<212> TYPE: DNA
<213> ORGANISM: Gallus gallus

<400> SEQUENCE: 49
ttattgtgct gtctcatcat tttggcaaag aattgtacca ccatggtgag caagggcgag       60
gagctgttca ccggggtggt gcccatcctg gtcgagctgg acggcgacgt aaacggccac      120
aagttcagcg tgtccggcga gggcgagggc gatgccacct acggcaagct gaccctgaag      180
ttcatctgca ccaccggcaa gctgcccgtg ccctggccca cactagtgac cacccttcgct     240 tacggcgtgc agtgcttcag ccgctacccc gaccacatga agcagcacga cttcttcaag      300
tccgccatgc ccgaaggcta cgtccaggag cgcaccatct tcttcaagga cgacggcaac      360
tacaagaccc gcgccgaggt gaagttcgag ggcgacaccc tggtgaaccg catcgagctg      420
aagggcatcg acttcaagga ggacggcaac atcctggggc acaagctgga gtacaacttc      480
aacagccaca acgtatacat catggccgac aagcagaaga acggcatcaa ggtgaacttc      540
aagatccgcc acaacatcga ggacggcagc gtgcagctcg ccgaccacta ccagcagaac      600 accccccatcg gcgacggccc cgtgctgctg                                      630

<210> SEQ ID NO 50
<211> LENGTH: 630
<212> TYPE: DNA
<213> ORGANISM: Gallus gallus

<400> SEQUENCE: 50
ttattgtgct gtctcatcat tttggcaaag aattgtacca ccatggtgag caagggcgag       60
gagctgttca ccggggtggt gcccatcctg gtcgagctgg acggcgacgt aaacggccac      120
aagttcagcg tgtccggcga gggcgagggc gatgccacct acggcaagct gaccctgaag      180
ttcatctgca ccaccggcaa gctgcccgtg ccctggccca cactagtgac cacccttcgct     240 tacggcgtgc agtgcttcag ccgctacccc gaccacatga agcagcacga cttcttcaag      300
tccgccatgc ccgaaggcta cgtccaggag cgcaccatct tcttcaagga cgacggcaac      360
tacaagaccc gcgccgaggt gaagttcgag ggcgacaccc tggtgaaccg catcgagctg      420
aagggcatcg acttcaagga ggacggcaac atcctggggc acaagctgga gtacaacttc      480
aacagccaca acgtatacat catggccgac aagcagaaga acggcatcaa ggtgaacttc      540
aagatccgcc acaacatcga ggacggcagc gtgcagctcg ccgaccacta ccagcagaac      600 accccccatcg gcgacggccc cgtgctgctg                                      630

<210> SEQ ID NO 51
<211> LENGTH: 630
<212> TYPE: DNA
<213> ORGANISM: Gallus gallus
```

<400> SEQUENCE: 51

```
ttattgtgct gtctcatcat tttggcaaag aattgtacca ccatggtgag caagggcgag      60
gagctgttca ccggggtggt gcccatcctg gtcgagctgg acggcgacgt aaacggccac     120
aagttcagcg tgtccggcga gggcgagggc gatgccacct acggcaagct gaccctgaag     180
ttcatctgca ccaccggcaa gctgcccgtg ccctggccca cactagtgac caccttcgct     240
tacggcgtgc agtgcttcag ccgctacccc gaccacatga agcagcacga cttcttcaag     300
tccgccatgc ccgaaggcta cgtccaggag cgcaccatct tcttcaagga cgacggcaac     360
tacaagaccc gcgccgaggt gaagttcgag ggcgacaccc tggtgaaccg catcgagctg     420
aagggcatcg acttcaagga ggacggcaac atcctggggc acaagctgga gtacaacttc     480
aacagccaca cgtatacat catggccgac aagcagaaga cggcatcaa ggtgaacttc       540
aagatccgcc acaacatcga ggacggcagc gtgcagctcg ccgaccacta ccagcagaac     600
accccccatcg gcgacggccc cgtgctgctg                                     630
```

<210> SEQ ID NO 52
<211> LENGTH: 630
<212> TYPE: DNA
<213> ORGANISM: Gallus gallus

<400> SEQUENCE: 52

```
ttattgtgct gtctcatcat tttggcaaag aattgtacca ccatggtgag caagggcgag      60
gagctgttca ccggggtggt gcccatcctg gtcgagctgg acggcgacgt aaacggccac     120
aagttcagcg tgtccggcga gggcgagggc gatgccacct acggcaagct gaccctgaag     180
ttcatctgca ccaccggcaa gctgcccgtg ccctggccca cactagtgac caccttcgct     240
tacggcgtgc agtgcttcag ccgctacccc gaccacatga agcagcacga cttcttcaag     300
tccgccatgc ccgaaggcta cgtccaggag cgcaccatct tcttcaagga cgacggcaac     360
tacaagaccc gcgccgaggt gaagttcgag ggcgacaccc tggtgaaccg catcgagctg     420
aagggcatcg acttcaagga ggacggcaac atcctggggc acaagctgga gtacaacttc     480
aacagccaca cgtatacat catggccgac aagcagaaga cggcatcaa ggtgaacttc       540
aagatccgcc acaacatcga ggacggcagc gtgcagctcg ccgaccacta ccagcagaac     600
accccccatcg gcgacggccc cgtgctgctg                                     630
```

<210> SEQ ID NO 53
<211> LENGTH: 630
<212> TYPE: DNA
<213> ORGANISM: Gallus gallus

<400> SEQUENCE: 53

```
ttattgtgct gtctcatcat tttggcaaag aattgtacca ccatggtgag caagggcgag      60
gagctgttca ccggggtggt gcccatcctg gtcgagctgg acggcgacgt aaacggccac     120
aagttcagcg tgtccggcga gggcgagggc gatgccacct acggcaagct gaccctgaag     180
ttcatctgca ccaccggcaa gctgcccgtg ccctggccca cactagtgac caccttcgct     240
tacggcgtgc agtgcttcag ccgctacccc gaccacatga agcagcacga cttcttcaag     300
tccgccatgc ccgaaggcta cgtccaggag cgcaccatct tcttcaagga cgacggcaac     360
tacaagaccc gcgccgaggt gaagttcgag ggcgacaccc tggtgaaccg catcgagctg     420
aagggcatcg acttcaagga ggacggcaac atcctggggc acaagctgga gtacaacttc     480
```

```
aacagccaca acgtatacat catggccgac aagcagaaga acggcatcaa ggtgaacttc        540
aagatccgcc acaacatcga ggacggcagc gtgcagctcg ccgaccacta ccagcagaac        600 accccccatcg gcgacggccc cgtgctgctg                                        630

<210> SEQ ID NO 54
<211> LENGTH: 448
<212> TYPE: DNA
<213> ORGANISM: Gallus gallus

<400> SEQUENCE: 54
aagagcagca gcagcagctc ctgtctcctg caggacagca gcagccctgc tcactccacg         60
agcacggtgg cagcagcagc agcgagcgca ccaccaggtc agtgccagtg aggggcccac        120
tgctccttgc tgcccaggca gcactgctgc tccatatgct gcctgcggcc acagggctgg        180
agtcccctct ccagcaactg catcatgctg ctggcgcagc tagtgagagg gaggaaacca        240
gtgttagtcc gtcatgtttc attattttca cttgaaaaat aaaattagct ctgaatagac        300
cagcactgca ttgaatttca tgggttgtgc tgcaagtagt gattcacaag gagttttct         360 cctttctacc aaaacacatt tcctcctgtg tttcttccaa tcctgtcaac cactcgttca        420
ctggctgctt gtctgcagag ctggagag                                          448

<210> SEQ ID NO 55
<211> LENGTH: 448
<212> TYPE: DNA
<213> ORGANISM: Gallus gallus

<400> SEQUENCE: 55
aagagcagca gcagcagctc ctgtctcctg caggacagca gcagccctgc tcactccacg         60
agcacggtgg cagcagcagc agcgagcgca ccaccaggtc agtgccagtg aggggcccac        120
tgctccttgc tgcccaggca gcactgctgc tccatatgct gcctgcggcc acagggctgg        180
agtcccctct ccagcaactg catcatgctg ctggcgcagc tagtgagagg gaggaaacca        240
gtgttagtcc gtcatgtttc attattttca cttgaaaaat aaaattagct ctgaatagac        300
cagcactgca ttgaatttca tgggttgtgc tgcaagtagt gattcacaag gagttttct         360 cctttctacc aaaacacatt tcctcctgtg tttcttccaa tcctgtcaac cactcgttca        420
ctggctgctt gtctgcagag ctggagag                                          448

<210> SEQ ID NO 56
<211> LENGTH: 448
<212> TYPE: DNA
<213> ORGANISM: Gallus gallus

<400> SEQUENCE: 56
aagagcagca gcagcagctc ctgtctcctg caggacagca gcagccctgc tcactccacg         60
agcacggtgg cagcagcagc agcgagcgca ccaccaggtc agtgccagtg aggggcccac        120
tgctccttgc tgcccaggca gcactgctgc tccatatgct gcctgcggcc acagggctgg        180
agtcccctct ccagcaactg catcatgctg ctggcgcagc tagtgagagg gaggaaacca        240
gtgttagtcc gtcatgtttc attattttca cttgaaaaat aaaattagct ctgaatagac        300
cagcactgca ttgaatttca tgggttgtgc tgcaagtagt gattcacaag gagttttct         360 cctttctacc aaaacacatt tcctcctgtg tttcttccaa tcctgtcaac cactcgttca        420
ctggctgctt gtctgcagag ctggagag                                          448
```

<210> SEQ ID NO 57
<211> LENGTH: 448
<212> TYPE: DNA
<213> ORGANISM: Gallus gallus

<400> SEQUENCE: 57

| | | | | | |
|---|---|---|---|---|---|
| aagagcagca | gcagcagctc | ctgtctcctg | caggacagca | gcagccctgc | tcactccacg | 60 |
| agcacggtgg | cagcagcagc | agcgagcgca | ccaccaggtc | agtgccagtg | aggggcccac | 120 |
| tgctccttgc | tgcccaggca | gcactgctgc | tccatatgct | gcctgcggcc | acagggctgg | 180 |
| agtcccctct | ccagcaactg | catcatgctg | ctggcgcagc | tagtgagagg | gaggaaacca | 240 |
| gtgttagtcc | gtcatgtttc | attattttca | cttgaaaaat | aaaattagct | ctgaatagac | 300 |
| cagcactgca | ttgaatttca | tgggttgtgc | tgcaagtagt | gattcacaag | gagttttttct | 360 |
| cctttctacc | aaaacacatt | tcctcctgtg | tttcttccaa | tcctgtcaac | cactcgttca | 420 |
| ctggctgctt | gtctgcagag | ctggagag | | | | 448 |

<210> SEQ ID NO 58
<211> LENGTH: 448
<212> TYPE: DNA
<213> ORGANISM: Gallus gallus

<400> SEQUENCE: 58

| | | | | | |
|---|---|---|---|---|---|
| aagagcagca | gcagcagctc | ctgtctcctg | caggacagca | gcagccctgc | tcactccacg | 60 |
| agcacggtgg | cagcagcagc | agcgagcgca | ccaccaggtc | agtgccagtg | aggggcccac | 120 |
| tgctccttgc | tgcccaggca | gcactgctgc | tccatatgct | gcctgcggcc | acagggctgg | 180 |
| agtcccctct | ccagcaactg | catcatgctg | ctggcgcagc | tagtgagagg | gaggaaacca | 240 |
| gtgttagtcc | gtcatgtttc | attattttca | cttgaaaaat | aaaattagct | ctgaatagac | 300 |
| cagcactgca | ttgaatttca | tgggttgtgc | tgcaagtagt | gattcacaag | gagttttttct | 360 |
| cctttctacc | aaaacacatt | tcctcctgtg | tttcttccaa | tcctgtcaac | cactcgttca | 420 |
| ctggctgctt | gtctgcagag | ctggagag | | | | 448 |

<210> SEQ ID NO 59
<211> LENGTH: 448
<212> TYPE: DNA
<213> ORGANISM: Gallus gallus

<400> SEQUENCE: 59

| | | | | | |
|---|---|---|---|---|---|
| aagagcagca | gcagcagctc | ctgtctcctg | caggacagca | gcagccctgc | tcactccacg | 60 |
| agcacggtgg | cagcagcagc | agcgagcgca | ccaccaggtc | agtgccagtg | aggggcccac | 120 |
| tgctccttgc | tgcccaggca | gcactgctgc | tccatatgct | gcctgcggcc | acagggctgg | 180 |
| agtcccctct | ccagcaactg | catcatgctg | ctggcgcagc | tagtgagagg | gaggaaacca | 240 |
| gtgttagtcc | gtcatgtttc | attattttca | cttgaaaaat | aaaattagct | ctgaatagac | 300 |
| cagcactgca | ttgaatttca | tgggttgtgc | tgcaagtagt | gattcacaag | gagttttttct | 360 |
| cctttctacc | aaaacacatt | tcctcctgtg | tttcttccaa | tcctgtcaac | cactcgttca | 420 |
| ctggctgctt | gtctgcagag | ctggagag | | | | 448 |

<210> SEQ ID NO 60
<211> LENGTH: 448
<212> TYPE: DNA
<213> ORGANISM: Gallus gallus

<400> SEQUENCE: 60

```
aagagcagca gcagcagctc ctgtctcctg caggacagca gcagccctgc tcactccacg    60
agcacggtgg cagcagcagc agcgagcgca ccaccaggtc agtgccagtg aggggcccac   120
tgctccttgc tgcccaggca gcactgctgc tccatatgct gcctgcggcc acagggctgg   180
agtcccctct ccagcaactg catcatgctg ctggcgcagc tagtgagagg gaggaaacca   240
gtgttagtcc gtcatgtttc attattttca cttgaaaaat aaaattagct ctgaatagac   300
cagcactgca ttgaatttca tgggttgtgc tgcaagtagt gattcacaag gagttttcct   360
cctttctacc aaaacacatt tcctcctgtg tttcttccaa tcctgtcaac cactcgttca   420
ctggctgctt gtctgcagag ctggagag                                     448
```

<210> SEQ ID NO 61
<211> LENGTH: 448
<212> TYPE: DNA
<213> ORGANISM: Gallus gallus

<400> SEQUENCE: 61

```
aagagcagca gcagcagctc ctgtctcctg caggacagca gcagccctgc tcactccacg    60
agcacggtgg cagcagcagc agcgagcgca ccaccaggtc agtgccagtg aggggcccac   120
tgctccttgc tgcccaggca gcactgctgc tccatatgct gcctgcggcc acagggctgg   180
agtcccctct ccagcaactg catcatgctg ctggcgcagc tagtgagagg gaggaaacca   240
gtgttagtcc gtcatgtttc attattttca cttgaaaaat aaaattagct ctgaatagac   300
cagcactgca ttgaatttca tgggttgtgc tgcaagtagt gattcacaag gagttttcct   360
cctttctacc aaaacacatt tcctcctgtg tttcttccaa tcctgtcaac cactcgttca   420
ctggctgctt gtctgcagag ctggagag                                     448
```

<210> SEQ ID NO 62
<211> LENGTH: 448
<212> TYPE: DNA
<213> ORGANISM: Gallus gallus

<400> SEQUENCE: 62

```
aagagcagca gcagcagctc ctgtctcctg caggacagca gcagccctgc tcactccacg    60
agcacggtgg cagcagcagc agcgagcgca ccaccaggtc agtgccagtg aggggcccac   120
tgctccttgc tgcccaggca gcactgctgc tccatatgct gcctgcggcc acagggctgg   180
agtcccctct ccagcaactg catcatgctg ctggcgcagc tagtgagagg gaggaaacca   240
gtgttagtcc gtcatgtttc attattttca cttgaaaaat aaaattagct ctgaatagac   300
cagcactgca ttgaatttca tgggttgtgc tgcaagtagt gattcacaag gagttttcct   360
cctttctacc aaaacacatt tcctcctgtg tttcttccaa tcctgtcaac cactcgttca   420
ctggctgctt gtctgcagag ctggagag                                     448
```

<210> SEQ ID NO 63
<211> LENGTH: 448
<212> TYPE: DNA
<213> ORGANISM: Gallus gallus

<400> SEQUENCE: 63

```
aagagcagca gcagcagctc ctgtctcctg caggacagca gcagccctgc tcactccacg    60
agcacggtgg cagcagcagc agcgagcgca ccaccaggtc agtgccagtg aggggcccac   120
```

| | |
|---|---|
| tgctccttgc tgcccaggca gcactgctgc tccatatgct gcctgcggcc acagggctgg | 180 |
| agtcccctct ccagcaactg catcatgctg ctggcgcagc tagtgagagg gaggaaacca | 240 |
| gtgttagtcc gtcatgtttc attattttca cttgaaaaat aaaattagct ctgaatagac | 300 |
| cagcactgca ttgaatttca tgggttgtgc tgcaagtagt gattcacaag gagttttctt | 360 |
| cctttctacc aaaacacatt tcctcctgtg tttcttccaa tcctgtcaac cactcgttca | 420 |
| ctggctgctt gtctgcagag ctggagag | 448 |

<210> SEQ ID NO 64
<211> LENGTH: 448
<212> TYPE: DNA
<213> ORGANISM: Gallus gallus

<400> SEQUENCE: 64

| | |
|---|---|
| aagagcagca gcagcagctc ctgtctcctg caggacagca gcagccctgc tcactccacg | 60 |
| agcacggtgg cagcagcagc agcgagcgca ccaccaggtc agtgccagtg aggggcccac | 120 |
| tgctccttgc tgcccaggca gcactgctgc tccatatgct gcctgcggcc acagggctgg | 180 |
| agtcccctct ccagcaactg catcatgctg ctggcgcagc tagtgagagg gaggaaacca | 240 |
| gtgttagtcc gtcatgtttc attattttca cttgaaaaat aaaattagct ctgaatagac | 300 |
| cagcactgca ttgaatttca tgggttgtgc tgcaagtagt gattcacaag gagttttctt | 360 |
| cctttctacc aaaacacatt tcctcctgtg tttcttccaa tcctgtcaac cactcgttca | 420 |
| ctggctgctt gtctgcagag ctggagag | 448 |

<210> SEQ ID NO 65
<211> LENGTH: 448
<212> TYPE: DNA
<213> ORGANISM: Gallus gallus

<400> SEQUENCE: 65

| | |
|---|---|
| aagagcagca gcagcagctc ctgtctcctg caggacagca gcagccctgc tcactccacg | 60 |
| agcacggtgg cagcagcagc agcgagcgca ccaccaggtc agtgccagtg aggggcccac | 120 |
| tgctccttgc tgcccaggca gcactgctgc tccatatgct gcctgcggcc acagggctgg | 180 |
| agtcccctct ccagcaactg catcatgctg ctggcgcagc tagtgagagg gaggaaacca | 240 |
| gtgttagtcc gtcatgtttc attattttca cttgaaaaat aaaattagct ctgaatagac | 300 |
| cagcactgca ttgaatttca tgggttgtgc tgcaagtagt gattcacaag gagttttctt | 360 |
| cctttctacc aaaacacatt tcctcctgtg tttcttccaa tcctgtcaac cactcgttca | 420 |
| ctggctgctt gtctgcagag ctggagag | 448 |

<210> SEQ ID NO 66
<211> LENGTH: 448
<212> TYPE: DNA
<213> ORGANISM: Gallus gallus

<400> SEQUENCE: 66

| | |
|---|---|
| aagagcagca gcagcagctc ctgtctcctg caggacagca gcagccctgc tcactccacg | 60 |
| agcacggtgg cagcagcagc agcgagcgca ccaccaggtc agtgccagtg aggggcccac | 120 |
| tgctccttgc tgcccaggca gcactgctgc tccatatgct gcctgcggcc acagggctgg | 180 |
| agtcccctct ccagcaactg catcatgctg ctggcgcagc tagtgagagg gaggaaacca | 240 |
| gtgttagtcc gtcatgtttc attattttca cttgaaaaat aaaattagct ctgaatagac | 300 |
| cagcactgca ttgaatttca tgggttgtgc tgcaagtagt gattcacaag gagttttctt | 360 |

```
ccttctacc aaaacacatt tcctcctgtg tttcttccaa tcctgtcaac cactcgttca    420
ctggctgctt gtctgcagag ctggagag                                      448

<210> SEQ ID NO 67
<211> LENGTH: 448
<212> TYPE: DNA
<213> ORGANISM: Gallus gallus

<400> SEQUENCE: 67
aagagcagca gcagcagctc ctgtctcctg caggacagca gcagccctgc tcactccacg    60
agcacggtgg cagcagcagc agcgagcgca ccaccaggtc agtgccagtg aggggcccac   120
tgctccttgc tgcccaggca gcactgctgc tccatatgct gcctgcggcc acagggctgg   180
agtcccctct ccagcaactg catcatgctg ctggcgcagc tagtgagagg gaggaaacca   240
gtgttagtcc gtcatgtttc attattttca cttgaaaaat aaaattagct ctgaatagac   300
cagcactgca ttgaatttca tgggttgtgc tgcaagtagt gattcacaag gagttttct    360 ccttctacc aaaacacatt tcctcctgtg tttcttccaa tcctgtcaac cactcgttca    420
ctggctgctt gtctgcagag ctggagag                                      448
```